(12) United States Patent
Sorge et al.

(10) Patent No.: US 6,645,761 B1
(45) Date of Patent: Nov. 11, 2003

(54) **HUMANIZED POLYNUCLEOTIDE SEQUENCE ENCODING *RENILLA MULLERI* GREEN FLUORESCENT PROTEIN**

(75) Inventors: Joseph A. Sorge, Wilson, WY (US); Peter Edward Vaillancourt, Del Mar, CA (US)

(73) Assignee: Stratagene, La Jolla, CA (US)

( * ) Notice: Subject to any disclaimer, the term of this patent is extended or adjusted under 35 U.S.C. 154(b) by 0 days.

(21) Appl. No.: 09/839,650

(22) Filed: Apr. 19, 2001

Related U.S. Application Data

(63) Continuation-in-part of application No. 09/748,786, filed on Dec. 22, 2000, now abandoned.

(51) Int. Cl.[7] .............................. C12N 5/10; C12N 1/00; C12N 15/12; C12N 15/63
(52) U.S. Cl. .................... 435/325; 435/243; 435/320.1; 435/410; 536/23.5
(58) Field of Search ...................... 536/23.5; 435/320.1, 435/325, 410, 243

(56) References Cited

U.S. PATENT DOCUMENTS

| | | |
|---|---|---|
| 5,968,750 A | 10/1999 | Zolotukhin et al. |
| 6,020,192 A * | 2/2000 | Muzyczka et al. ........ 435/320.1 |
| 6,232,107 B1 | 5/2001 | Bryan et al. |

FOREIGN PATENT DOCUMENTS

| | | |
|---|---|---|
| WO | 99/49019 | 9/1999 |
| WO | WO 99/49019 | 9/1999 |
| WO | 01/68824 A2 | 9/2001 |

OTHER PUBLICATIONS

Sergei Zolotukhin et al, A "Humanized" Green Fluorescent Protein cDNA Adapted for High–Level Expression in Mammalian Cells, Journal Of Virology Jul. 1996, pp. 4646–4654.*

Copy of the International Search Report (PCT/US01/49091).

* cited by examiner

*Primary Examiner*—Terry McKelvey
(74) *Attorney, Agent, or Firm*—Palmer & Dodge LLP; Kathleen M. William

(57) ABSTRACT

The present invention provides a polynucleotide encoding a green fluorescent protein from *Renilla mulleri* comprising a humanized sequence which permits enhanced expression of the encoded polypeptide in mammalian cells.

3 Claims, 10 Drawing Sheets

SEQ ID NO: 1

ATGGTGAGCAAGCAGATCCTGAAGAACACCTGCCTGCAGGAGGTGATGAGCTACAA
GGTGAACCTGGAGGGCATCGTGAACAACCACGTGTTACCATGGAGGGCTGCGGGCA
AGGGCAACATCCTGTTCGGCAACCAGTGGTGCAGATCCGCGTGACCAAGGGCGCC
CCCCTGCCCTTCGCCTTCGACATCGTGAGCCCCTTCCAGTACGGCAACCGCACC
TTCACCAAGTACCCCAACGACTACTTCATCCAGAGCTTCCCGCCCGGC
TTCATGTACGAGCGCACCCTGCGCTACGAGGACAAGTTCGTGTACCGTGGAGATCCGGCAG
CGACATCAACCTGATGAGGACAAGTTCGTGTACCGCGTGGAGTACAAGGGCAGCA
ACTTCCCCGACGACGCCCGTGATGCAGAGACCATCCTGGGCATCGAGCCCAGC
TTCGAGGCCATGTACATGAACAACGGCAAGTACTACAGTGCCACATGAAGACCCTGATGAAGAGCA
CAAGCTGAACAGCGGCAAGTTCCCCCTCCTACCACTTCATCCAGCACGCCTGGAGAAG
AGGGCGTGGTGAAGGAGAGTTCGTGGAGCAGCAGGACGGGACCATCGCCCAGAT
ACCTACGTGGAGGACGGGCTTCGTGGAGCAGCAGGACGAGACCATCGCCCCAGAT
GACCAGCATCGGCCAAGCCCTGGCCAGCCTGCACGAGTGGGTGTAA

FIG. 1

```
GGTTATACAC AAGTGTATCG CGTATCTGCA GACGCATCTA GTGGGATTAT TCGAGCGGTA   60
GTATTTACGT CAGACCTGTC TAATCGAAAC CACAACAAAC TCTTAAAATA AGCCACATTT  120
ACATAATATC TAAGAGACGC CTCATTTAAG AGTAGTAAAA ATATAATATA TGATAGAGTA  180
TACAACTCTC GCCTTAGACA GACAGTGTGC AACAGAGTAA CTCTTGTTAA TGCAATCGAA  240
AGCGTCAAGA GAGATAAG ATG AGT AAA CAA ATA TTG AAG AAC ACT TGT TTA    291
                    Met Ser Lys Gln Ile Leu Lys Asn Thr Cys Leu
                     1           5                      10
```

```
CAA GAA GTA ATG TCG TAT AAA GTA AAT CTG GAA GGA ATT GTA AAC AAC   339
Gln Glu Val Met Ser Tyr Lys Val Asn Leu Glu Gly Ile Val Asn Asn
             15                  20                  25
CAT GTT TTT ACA ATG GAG GGT TGC GGC AAA GGG AAT ATT TTA TTC GGC   387
His Val Phe Thr Met Glu Gly Cys Gly Lys Gly Asn Ile Leu Phe Gly
             30                  35                  40
AAT CAA CTG GTT CAG ATT CGT GTC ACG AAA GGG GCC CCA CTG CCT TTT   435
Asn Gln Leu Val Gln Ile Arg Val Thr Lys Gly Ala Pro Leu Pro Phe
             45                  50                  55
GCA TTT GAT ATT GTG TCA CCA GCT TTT CAA TAT GGC AAC CGT ACT TTC   483
Ala Phe Asp Ile Val Ser Pro Ala Phe Gln Tyr Gly Asn Arg Thr Phe
60                  65                  70                  75
ACG AAA TAT CCG AAT GAT ATA TCA GAT TAT TTT ATA CAA TCA TTT CCA   531
Thr Lys Tyr Pro Asn Asp Ile Ser Asp Tyr Phe Ile Gln Ser Phe Pro
             80                  85                  90
GCA GGA TTT ATG TAT GAA CGA ACA TTA CGT TAC GAA GAT GGC GGA CTT   579
Ala Gly Phe Met Tyr Glu Arg Thr Leu Arg Tyr Glu Asp Gly Gly Leu
             95                 100                 105
GTT GAA ATT CGT TCA GAT ATA AAT TTA ATA GAA GAC AAG TTC GTC TAC   627
Val Glu Ile Arg Ser Asp Ile Asn Leu Ile Glu Asp Lys Phe Val Tyr
AGA GTG GAA TAC AAA GGT AGT AAC TTC CCA GAT GAT GGT CCC GTC ATG   675
Arg Val Glu Tyr Lys Gly Ser Asn Phe Pro Asp Asp Gly Pro Val Met
        125                 130                 135
CAG AAG ACT ATC TTA GGA ATA GAG CCT TCA TTT GAA GCC ATG TAC ATG   723
Gln Lys Thr Ile Leu Gly Ile Glu Pro Ser Phe Glu Ala Met Tyr Met
140                 145                 150                 155
AAT AAT GGC GTC TTG GTC GGC GAA GTA ATT CTT GTC TAT AAA CTA AAC   771
Asn Asn Gly Val Leu Val Gly Glu Val Ile Leu Val Tyr Lys Leu Asn
                160                 165                 170
TCT GGG AAA TAT TAT TCA TGT CAC ATG AAA ACA TTA ATG AAG TCG AAA   819
Ser Gly Lys Tyr Tyr Ser Cys His Met Lys Thr Leu Met Lys Ser Lys
            175                 180                 185
GGT GTA GTA AAG GAG TTT CCT TCG TAT CAT TTT ATT CAA CAT CGT TTG   867
Gly Val Val Lys Glu Phe Pro Ser Tyr His Phe Ile Gln His Arg Leu
        190                 195                 200
GAA AAG ACT TAC GTA GAA GAC GGG GGG TTC GTT GAA CAG CAT GAG ACT   915
Glu Lys Thr Tyr Val Glu Asp Gly Gly Phe Val Glu Gln His Glu Thr
        205                 210                 215
GCT ATT GCT CAA ATG ACA TCT ATA GGA AAA CCA CTA GGA TCC TTA CAC   963
Ala Ile Ala Gln Met Thr Ser Ile Gly Lys Pro Leu Gly Ser Leu His
220                 225                 230                 235
GAA TGG GTT TAA ACACAGTTAC ATTACTTTTT CCAATTCGTG TTTCATGTCA AATAAT 1021
Glu Trp Val *
```

FIG. 2

```
Met Ser Lys Gln Ile Leu Lys Asn Thr Cys Leu Gln Glu Val Met Ser
 1            5                  10                 15
Tyr Lys Val Asn Leu Glu Gly Ile Val Asn Asn His Val Phe Thr Met
            20                  25                 30
Glu Gly Cys Gly Lys Gly Asn Ile Leu Phe Gly Asn Gln Leu Val Gln
            35                  40                 45
Ile Arg Val Thr Lys Gly Ala Pro Leu Pro Phe Ala Phe Asp Ile Val
            50                  55                 60
Ser Pro Ala Phe Gln Tyr Gly Asn Arg Thr Phe Thr Lys Tyr Pro Asn
65                  70                  75                 80
Asp Ile Ser Asp Tyr Phe Ile Gln Ser Phe Pro Ala Gly Phe Met Tyr
            85                  90                 95
Glu Arg Thr Leu Arg Tyr Glu Asp Gly Gly Leu Val Glu Ile Arg Ser
            100                 105                110
Asp Ile Asn Leu Ile Glu Asp Lys Phe Val Tyr Arg Val Glu Tyr Lys
            115                 120                125
Gly Ser Asn Phe Pro Asp Asp Gly Pro Val Met Gln Lys Thr Ile Leu
    130                 135                140
Gly Ile Glu Pro Ser Phe Glu Ala Met Tyr Met Asn Asn Gly Val Leu
145                 150                 155                160
Val Gly Glu Val Ile Leu Val Tyr Lys Leu Asn Ser Gly Lys Tyr Tyr
                165                 170                175
Ser Cys His Met Lys Thr Leu Met Lys Ser Lys Gly Val Val Lys Glu
            180                 185                190
Phe Pro Ser Tyr His Phe Ile Gln His Arg Leu Glu Lys Thr Tyr Val
            195                 200                205
Glu Asp Gly Gly Phe Val Glu Gln His Glu Thr Ala Ile Ala Gln Met
    210                 215                220
Thr Ser Ile Gly Lys Pro Leu Gly Ser Leu His Glu Trp Val
225                 230                 235
```

FIG. 3

| FIG. 4A |
|---------|
| FIG. 4B |
| FIG. 4C |

FIG. 4

```
            M   V   S       K   Q   I   L   K   N   T   C   L   Q   E   V   M   S   Y   K   V
wt:    1    ATG---AGTAAACAAATATTGAAGAACACTTGTTTACAAGAAGTAATGTCGTATAAAGTA     60
            |||   |||||||| || || ||||| |||||| |||||||  ||| || || ||||| |
hmGFP: 1    ATGGTGAGCAAGCAGCAGATCCTGAAGAACACCTGCCTGCAGGAGGTGATGAGCTACAAGGTG  60

N   L   E   G   I   V   N   N   H   V   F   T   M   E   G   C   G   K   G   N
wt:    61   AATCTGGAAGGAATTGTAAACAACCATGTTTTTACAATGGAGGGTTGCGGCAAAGGGAAT   120
            || ||||| || ||||| || ||||| ||||| ||||| ||||| ||| |||| ||| |
hmGFP: 61   AACCTGGAGGGCATCGTGAACAACCACGTGTTCACCATGGAGGGCTGCGGCAAGGGCAAC   120

I   L   F   G   N   Q   L   V   Q   I   R   V   T   K   G   A   P   L   P   F
wt:    121  ATTTTATTCGGCAATCAACTGGTTCAGATTCGTGTCACGAAAGGGCCCCACTGCCTTTT    180
            || ||  |||| |||||||| |||||| ||||| |||| ||| |||| ||||||  |||
hmGFP: 121  ATCCTGTTCGGCAACCAGCTGGTGCAGATCCGCGTGACCAAGGGCGCCCCCCTGCCCTTC   180
```

FIG. 4A

```
           A  F  D  I  V  S  P  A  F  Q  Y  G  N  R  T  F  T  K  Y  P
wt:    181 GCATTTGATATTGTGTCACCAGCTTTTCAATATGGCAACCGTACTTTCACGAAATATCCG 240
           || ||| ||  || || || ||  ||| |  ||||| ||  || || ||||  ||  ||
hmGFP: 181 GCCTTCGACATCGTGAGCCCCGCCTTCCAGTACGGCAACCGCACCTTCACCAAGTACCCC 240

N  D  I  S  D  Y  F  I  Q  S  F  P  A  G  F  M  Y  E  R  T
wt:    241 AATGATATATCAGATTATTTTATACAATCATTTCCAGCAGGATTTATGTATGAACGAACA 300
           || ||| |  |  || ||  |  || || || || || || || ||| |||||| |||
hmGFP: 241 AACGATATCAGCGACTACTTCATACAGAGCTTCCCGGCTTCCATGTACGAGCGCACC 300

L  R  Y  E  D  G  G  L  V  E  I  R  S  D  I  N  L  I  E  D
wt:    301 TTACGTTACGAAGATGGCGGACTTGTTGAAATTCGTTCAGATATAAATTTAATAGAAGAC 360
           || || ||||| ||||| ||    ||  || ||| |  || |||  ||| | |||||||
hmGFP: 301 CTGCGCTACGAGGACGGCGGCCTGGTGGAGATCCGCAGCGACATCAACCTGATCGAGGAC 360

K  F  V  Y  R  V  E  Y  K  G  S  N  F  P  D  D  G  P  V  M
wt:    361 AAGTTCGTTTACAGAGTGGAATACAAAGGTAGTAACTTCCCAGATGATGGTCCCGTCATG 420
           ||||||||| || ||||| || ||||| || ||||| |||  ||||||| |||  ||||
hmGFP: 361 AAGTTCGTGTACCGCGTGGAGTACAAGGGCAGCAACTTCCCCGACGACGGCCCCGTGATG 420

Q  K  T  I  L  G  I  E  P  S  F  E  A  M  Y  M  N  N  G  V
wt:    421 CAGAAGACTATCTTAGGAATAGAGCCTTCATTTGAAGCCATGTACATGAATAATGGCGTC 480
           |||||||| ||| | || || ||||| || || ||||| |||||||| ||||||||||
hmGFP: 421 CAGAAGACCATCCTGGGCATCGAGCCCAGCTTCGAGGCCATGTACATGAACAACGGCGTG 480
```

FIG. 4B

```
            L   V  G  E   V  I   L   V  Y  K   L  N   S  G  K   Y  Y   S  C  H
wt:    481  TTGGTCGGCGAAGTAATTCTTGTCTATAAACTAAACTCTGGGAAATATTATTCATGTCAC  540
            ||||  |||| |||||  ||   |||| ||   ||||  | ||  ||||   ||| |||
hmGFP: 481  CTGGTGGGCGAGGTGATCCTGGTGGAGCTGGACGGCGACGTAAACGGCCACAAGTTCAGC  540

M  K  T  L  M  K  S   K  G   V  V   K  E   F  P   S  Y   H  F  I
wt:    541  ATGAAAACATTAATGAAGTCGAAAGGTGTAGTAAAGGAGTTTCCTTCGTATCATTTTATT  600
            ||||| ||| || |||| |||| ||||| || |||||| || || |||  ||  ||
hmGFP: 541  ATGAAGACCCTGATGAAGAGCAAGGGCGTGGTGAAGGAGTTCCCCTCCTACCACTTCATC  600

Q  H  R  L   E  K  T   Y  V   E  D  G   G  F   V  E  Q   H  E  T
wt:    601  CAACATCGTTTGGAAAAGACTTACGTAGAAGACGGAGGTGTTCGTTGAACAGCATGAGACT  660
            |||||| || |||||||||||  || |||||||| ||| |  ||||||||||||| |||
hmGFP: 601  CAGCACCGCCTGGAGAAGACCTACGTGGAGGACGGCGGCGTGCTGACCGGCAGCAGCGAGACC  660

A  I   A  Q   M  T   S  I  G  K   P  L   G  S  L   H  E  W  V  stop
wt:    661  GCTATTGCTCAAATGACATCTATAGGAAAACCACTAGGATCCTTACACGAATGGGTTTAA  720
            || ||  |  |  |||||  |  || |||||||  ||||  | || ||||||  |||||
hmGFP: 661  GCCATCGCCCAGATGACCAGCATCGGCAAGCCCCTGGGCAGCCTGCACGAGTGGGTGTAA  720
```

FIG. 4C

HUMANIZED POLYNUCLEOTIDE SEQUENCE ENCODING *RENILLA MULLERI* GREEN FLUORESCENT PROTEIN

This application is a continuation-in-part of U.S. patent application Ser. No. 09/748,786, filed Dec. 22, 2000, now abandoned, incorporated herein by reference in its entirety.

BACKGROUND OF THE INVENTION

The green fluorescent protein (GFP) from the jellyfish *Aequorea victoria* has become an extremely useful tool for tracking and quantifying biological entities in the fields of biochemistry, molecular and cell biology, and medical diagnostics (Chalfie et al., 1994, Science 263: 802–805; Tsien, 1998, Ann, Rev. Biochem. 67: 509–544). There are no cofactors or substrates required for fluorescence, thus the protein can be used in a wide variety of organisms and cell types. GFP has been used as a reporter gene to study gene expression in vivo by insertion downstream of a test promoter. The protein has also been used to study the subcellular localization of a number of proteins by direct fusion of the test protein to GFP, and GFP has become the reporter of choice for monitoring the infection efficiency of viral vectors both in cell culture and in animals. In addition, a number of genetic modifications have been made to GFP resulting in variants for which spectral shifts correspond to changes in the cellular environment such as pH, ion flux, and the phosphorylation state of the cell. Perhaps the most promising role for GFP as a cellular indicator is its application to fluorescence resonance energy transfer (FRET) technology. FRET occurs with fluorophores for which the emission spectrum of one overlaps with the excitation spectrum of the second. When the fluorophores are brought into close proximity, excitation of the "donor" fluorophore results in emission from the "acceptor". Pairs of such fluorophores are thus useful for monitoring molecular interactions. Fluorescent proteins such as GFP are useful for analysis of protein:protein interactions in vivo or in vitro if their fluorescent emission and excitation spectra overlap to allow FRET. The donor and acceptor fluorescent proteins may be produced as fusions with the proteins one wishes to analyze for interactions. These types of applications of GFPs are particularly appealing for high throughput analyses, since the readout is direct and independent of subcellular localization.

Purified *A. victoria* GFP is a monomeric protein of about 27 kDa that absorbs blue light with excitation wavelength maximum of 395 nm, with a minor peak at 470 nm, and emits green fluorescence with an emission wavelength of about 510 nm and a minor peak near 540 nm (Ward et al., 1979, Photochem. Photobiol. Rev. 4: 1–57). The excitation maximum of *A. victoria* GFP is not within the range of wavelengths of standard fluorescein detection optics. Further, the breadth of the excitation and emission spectra of the *A. victoria* GFP are not well suited for use in applications involving FRET. In order to be useful in FRET applications, the excitation and emission spectra of the fluorophores are preferably tall and narrow, rather than low and broad. There is a need in the art for GFP proteins that are amenable to the use of standard fluorescein excitation and detection optics. There is also a need in the art for GFP proteins with narrow, preferably non-overlapping spectral peaks.

The use of *A. victoria* GFP as a reporter for gene expression studies, while very popular, is hindered by relatively low quantum yield (the brightness of a fluorophore is determined as the product of the extinction coefficient and the fluorescence quantum yield). Generally, the *A. victoria* GFP coding sequences must be linked to a strong promoter, such as the CMV promoter or strong exogenous regulators such as the tetracycline transactivator system, in order to produce readily detectable signal. This makes it difficult to use GFP as a reporter for examining the activity of native promoters responsive to endogenous regulators. Higher intensity would obviously also increase the sensitivity of other applications of GFP technology. There is a need in the art for GFP proteins with higher quantum yield.

Another disadvantage of *A. victoria* GFP involves fluctuations in its spectral characteristics with changes in pH. At high pH (pH 11–12), the wild-type *A. victoria* GFP loses absorbance and excitation amplitude at 395 nm and gains amplitude at 470 nm (Ward et al., 1982, Photochem. Photobiol. 35: 803–808). *A. victoria* fluorescence is also quenched at acid pH, with a pKa around 4.5. There is a need in the art for GFPs exhibiting fluorescence that is less sensitive to pH fluctuations.

Further, in order to be more useful in a broad range of applications, there is a need in the art for GFP proteins exhibiting increased stability of fluorescence characteristics relative to *A. victoria* GFP, with regard to organic solvents, detergents and proteases often used in biological studies. There is also a need in the art for GFP proteins that are more likely to be soluble in a wider range of cell types and less likely to interfere non-specifically with endogenous proteins than *A. victoria* GFP.

A number of modifications to *A. victoria* GFP have been made with the aim of enhancing the usefulness of the protein. For example, modifications aimed at enhancing the brightness of the fluorescence emissions or the spectral characteristics of either the excitation or emission spectra or both have been made. It is noted that the stated aim of several of these modification approaches was to make an *A. victoria* GFP that is more similar to *R. reniformis* GFP in its excitation and emission spectra and fluorescence intensity.

Literature references relating to *A. victoria* mutants exhibiting altered fluorescence characteristics include, for example, the following. Heim et al. (1995, Nature 373: 663–664) relates to mutations at S65 of *A. victoria* that enhance fluorescence intensity of the polypeptide. The S65T mutation to the *A. victoria* GFP is said to "ameliorate its main problems and bring its spectra much closer to that of Renilla".

A review by Chalfie (1995, Photochem. Photobiol. 62: 651–656) notes that an S65T mutant of *A. victoria*, the most intensely fluorescent mutant of *A. victoria* known at the time, is not as intense as the *R. reniformis* GFP.

Further references relating to *A. victoria* mutants include, for example, Ehrig et al., 1995, FEBS Lett. 367: 163–166); Surpin et al., 1987, Photochem. Photobiol. 45 (Suppl): 95S; Delagrave et al., 1995, BioTechnology 13: 151–154; and Yang et al., 1996, Gene 173: 19–23.

Patent and patent application references relating to *A. victoria* GFP and mutants thereof include the following. U.S. Pat. No. 5,874,304 discloses *A. victoria* GFP mutants said to alter spectral characteristics and fluorescence intensity of the polypeptide. U.S. Pat. No. 5,968,738 discloses *A. victoria* GFP mutants said to have altered spectral characteristics. One mutation, V163A, is said to result in increased fluorescence intensity. U.S. Pat. No. 5,804,387 discloses *A. victoria* mutants said to have increased fluorescence intensity, particularly in response to excitation with 488 nm laser light. U.S. Pat. No. 5,625,048 discloses *A. victoria* mutants said to have altered spectral characteristics as well as several mutants said to have increased fluorescence intensity. Related U.S. Pat. No. 5,777,079 discloses further combinations of mutations said to provide *A. victoria* GFP polypeptides with increased fluorescence intensity. International Patent Application (PCT) No. W098/21355 discloses *A. victoria* GFP mutants said to have increased fluorescence intensity, as do W097/20078, W097/42320 and W097/11094. PCT Application No. W098/06737 discloses mutants said to have altered spectral characteristics, several of which are said to have increased fluorescence intensity.

In addition to *A. victoria*, GFPs have been identified in a variety of other coelenterates and anthazoa, however only three GFPs have been cloned, those from *A. victoria* (Prasher, 1992, Gene 111: 229–233) and from the sea pansies, *Renilla mulleri* (WO 99/49019) and *Renilla reniformis* (Felts et al. (2000) Strategies 13:85). One common drawback that all three of the cloned GFPs share is relatively poor expression in mammalian cells.

SUMMARY OF THE INVENTION

The present invention provides a humanized polynucleotide encoding *R. mulleri* GFP.

In a preferred embodiment, the polynucleotide comprises the sequence of SEQ ID NO: 1.

In one embodiment, the invention provides a recombinant vector comprising a humanized polynucleotide encoding *R. mulleri* GFP.

In a further embodiment, the recombinant vector is contained within a cell.

The present invention further provides a method of producing *R. mulleri* GFP comprising the steps of: introducing a recombinant vector comprising a humanized polynucleotide sequence encoding *R. mulleri* GFP to a cell; culturing the cell; and isolating *R. mulleri* GFP from the cell.

In one embodiment, the cell is a mammalian cell.

In a preferred embodiment, the cell is a human cell.

The present invention further provides a method of determining the location of a polypeptide of interest in a cell, the method comprising the steps of: linking said polynucleotide sequence encoding a polypeptide of interest with a humanized polynucleotide encoding *R. mulleri* GFP, such that the linked polynucleotide sequences are fused in frame; introducing the linked polynucleotide sequences to a cell; and determining the location of the polypeptide encoded by the linked polynucleotide sequences.

The invention also provides a method of identifying cells to which a recombinant vector has been introduced, the method comprising the steps of: introducing a recombinant vector to a population of cells, wherein the recombinant vector comprises a humanized polynucleotide which encodes *R. mulleri* GFP and the cells permit expression of said humanized polynucleotide; illuminating the cell population with light within the excitation spectrum of *R. mulleri* GFP; and detecting fluorescence in the emission spectrum of *R. mulleri* GFP in the cell population, thereby identifying a cell to which said recombinant vector has been introduced.

In one embodiment, the GFP is expressed as a fusion polypeptide.

In a further embodiment, the GFP is expressed as a distinct polypeptide.

In one embodiment, the cells are identified by FACS analysis.

The invention further provides a method of monitoring the activity of a transcriptional regulatory sequence, the method comprising the steps of: operably linking a nucleic acid sequence comprising the transcriptional regulatory sequence to a humanized nucleic acid sequence encoding *R. mulleri* GFP to form a reporter construct; introducing the reporter construct to a cell; and detecting *R. mulleri* GFP fluorescence in the cell, wherein the fluorescence reflects the activity of the transcriptional regulatory sequence.

The invention still further provides a method of detecting a modulator of a transcriptional regulatory sequence, the method comprising the steps of: operably linking a nucleic acid sequence comprising the transcriptional regulatory sequence to a humanized nucleic acid sequence encoding *R. mulleri* GFP to form a reporter construct, wherein the transcriptional regulatory sequence is responsive to the presence of the modulator; introducing the reporter construct to a cell; and detecting *R. mulleri* GFP fluorescence in the cell, wherein the fluorescence indicates the presence of the modulator.

The invention still further provides a method of screening for an inhibitor of a transcriptional regulatory sequence, the method comprising the steps of: operably linking a nucleic acid sequence comprising the transcriptional regulatory sequence to a humanized nucleic acid sequence encoding *R. mulleri* GFP to form a reporter construct; introducing the reporter construct to a cell; contacting the cell with a candidate inhibitor of the transcriptional regulatory sequence; and detecting *R. mulleri* GFP fluorescence in the cell, wherein a decrease in the fluorescence relative to that detected in the absence of the candidate inhibitor indicates that the candidate inhibitor inhibits the activity of the transcriptional regulatory sequence.

The invention still further provides a method of producing a fluorescent molecular weight marker, the method comprising the steps of: linking a humanized nucleic acid sequence encoding *R. mulleri* GFP in frame to a nucleic acid sequence encoding a polypeptide of known relative molecular weight such that the linked molecules encode a fusion polypeptide; introducing the linked nucleic acid sequences to a cell; isolating said fusion polypeptide from the cell, wherein the fusion polypeptide is a relative molecular weight marker.

In one embodiment, the cell is a mammalian cell.

In a further embodiment, the cell is a human cell.

In a still further embodiment, the humanized nucleic acid sequence encoding *R. mulleri* GFP is the sequence of SEQ ID NO: 1.

The term "humanized *R. mulleri* polynucleotide" or "humanized *R. mulleri* GFP sequence" refers to a polynucleotide coding sequence in which at least 179 codons of the polynucleotide coding sequence for a non-human polypeptide (i.e., a polypeptide not naturally expressed in humans) have been altered to a codon sequence more preferred for expression in mammalian cells (i.e., SEQ ID NO: 1). In the "humanized *R. mulleri* GFP nucleotide sequence of SEQ ID NO: 1, residue number 93 may be either a T or a C. In addition, an equivalent of a humanized sequence according to the invention is contempalted which is a polynucleotide according to SEQ ID NO: 1 in which one, two, three, four, five, six, seven, eight, nine, ten, eleven, twelve, thirteen, fourteen, fifteen, sixteen, seventeen, eighteen, nineteen, or twenty of those 179 codons that are altered to be humanized codons in SEQ ID NO: 1 are not altered such that they are humanized codons (that is, are not preferred in mammalian, particularly human, cells), provided expression in mammalian cells of the equivalent "humanized *R. mulleri* polynucleotide" described in SEQ ID NO: 1 is not reduced (relative to expression of the humanized sequence of SEQ ID NO: 1 in the same type of cells) by more than 5% or at most 10%.

The amount of fluorescent polypeptide expressed in a human cell from a humanized GFP polynucleotide sequence is at least two-fold greater, on either a mass or a fluorescence intensity scale per cell, than the amount expressed from an equal amount or number of copies of a wild type R. mulleri GFP polynucleotide.

As used herein, the term "humanized codon" means a codon, within a polynucleotide sequence encoding a non-human polypeptide, that has been changed to a codon that is more preferred for expression in human cells relative to that codon encoded by the non-human organism from which the non-human polypeptide is derived. Species-specific codon preferences stem in part from differences in the expression of tRNA molecules with the appropriate anticodon sequence. That is, one factor in the species-specific codon preference is the relationship between a codon and the amount of corresponding anticodon tRNA expressed.

It should be understood that any of the recombinant vectors of the invention or cells containing such a vector will comprise a humanized polynucleotide encoding R. mulleri GFP.

The wild type "R. mulleri green fluorescent protein" or "R. mulleri GFP" is encoded by the nucleic acid sequence of SEQ ID NO: 2 (WO 99/49019, incorporated herein by reference).

As used herein, the term "wild-type R. mulleri GFP" refers to a polypeptide of SEQ ID NO: 3 (WO 99/49019).

The term "variant thereof" when used in reference to an R. mulleri GFP means that the amino acid sequence bears one or more residue differences relative to the wild type R. mulleri GFP sequence and has the identical biological activity (fluorescence intensity) of the wild type polypeptide.

As used herein, the term "increased fluorescence intensity" or "increased brightness" refers to fluorescence intensity or brightness that is greater than that exhibited by wild-type R. mulleri GFP under a given set of conditions. Generally, an increase in fluorescence intensity or brightness means that fluorescence of a variant is at least 5% or more, and preferably 10%, 20%, 50%, 75%, 100% or more, up to even 5 times, 10 times, 20 times, 50 times or 100 times or more intense or bright than wild-type R. mulleri GFP under a given set of conditions.

As used herein, the term "fused heterologous polypeptide domain" refers to an amino acid sequence of two or more amino acids fused in frame to R. mulleri GFP. A fused heterologous domain may be linked to the N or C terminus of the R. mulleri GFP polypeptide.

As used herein, the term "fused to the amino-terminal end" refers to the linkage of a polypeptide sequence to the amino terminus of another polypeptide. The linkage may be direct or may be mediated by a short (e.g., about 2–20 amino acids) linker peptide.

As used herein, the term "fused to the carboxy-terminal end" refers to the linkage of a polypeptide sequence to the carboxyl terminus of another polypeptide. The linkage may be direct or may be mediated by a linker peptide.

As used herein, the term "linker sequence" refers to a short (e.g., about 1–20 amino acids) sequence of amino acids that is not part of the sequence of either of two polypeptides being joined. A linker sequence is attached on its amino-terminal end to one polypeptide or polypeptide domain and on its carboxyl-terminal end to another polypeptide or polypeptide domain.

As used herein, the term "excitation spectrum" refers to the wavelength or wavelengths of light that, when absorbed by a fluorescent polypeptide molecule of the invention, causes fluorescent emission by that molecule.

As used herein, the term "emission spectrum" refers to the wavelength or wavelengths of light emitted by a fluorescent polypeptide.

As used herein, the terms "distinguishable" or "detectably distinct" mean that standard filter sets allow either the excitation of one form of a polypeptide without excitation of another given polypeptide, or similarly, that standard filter sets allow the distinction of the emission from one polypeptide form from the emission spectrum of another. Generally, distinguishable or detectably distinct excitation or emission spectra have peaks that vary by more than 1 nm, and preferably vary by more than 2, 3, 4, 5, 10 or more nm.

As used herein, the term "fusion polypeptide" refers to a polypeptide that is comprised of two or more amino acid sequences, from two or more proteins that are not found linked in nature, that are physically linked by a peptide bond. As used herein, only one protein which comprises a "fusion polypeptide" of the present invention is a fluorescent protein.

As used herein, the term "emission spectrum overlaps the excitation spectrum" means that light emitted by one fluorescent polypeptide is of a wavelength or wavelengths that causes excitation and emission by another fluorescent polypeptide.

As used herein, the term "population of cells" refers to a plurality of cells, preferably, but not necessarily of same type or strain.

As used herein the term "distinct polypeptide" refers to a polypeptide that is not expressed as a fusion polypeptide.

As used herein, the term "FACS analysis" refers to the method of sorting cells, fluorescence activated cell sorting, wherein cells are stained with or express one or more fluorescent markers. In this method, cells are passed through an apparatus that excites and detects fluorescence from the marker(s). Upon detection of fluorescence in a given portion of the spectrum by a cell, the FACS apparatus allows the separation of that cell from those not expressing that fluorescence spectrum.

As used herein, the term "lipid soluble transcriptional modulator" refers to a composition that is capable of passing through cell membranes (nuclear or cytoplasmic) and has a positive or negative effect on the transcription of one or more genes or constructs.

As used herein, the term "operably linked" means that a given coding sequence is joined to a given transcriptional regulatory sequence such that transcription of the coding sequence occurs and is regulated by the regulatory sequence.

As used herein, the term "reporter construct" refers to a polynuclectide construct encoding a detectable molecule, linked to a transcriptional regulatory sequence conferring regulated transcription upon the polynucleotide encoding the detectable molecule. A detectable molecule is preferably an R. mulleri GFP.

As used herein, the term "responsive to the presence of a modulator" means that a given transcriptional regulatory sequence is either turned on or turned off in the presence of a given compound. As used herein, gene expression is "turned on" when the polypeptide encoded by the gene sequence (e.g., a GFP polypeptide) is detectable over background, or alternatively, when the polypeptide is detectable in an increased amount over the amount detected in the absence of a given modulator compound. In this context, "increased amount" means at least 10%, preferably 20%, 50%, 75%, 100% or more, up to even 5 times, 10 times, 20 times, 50 times, or 100 times or more higher than background detection, with background detection being the amount of signal observed in the absence of the modulator compound.

As used herein, the term "modulator of a transcriptional regulatory sequence" refers to a compound or chemical moiety that causes a change in the level of expression from a transcriptional regulatory sequence. Preferably, the change is detectable as an increase or decrease in the detection of a reporter molecule or reporter molecule activity, with at least 10%, 20%, 50%, 75%, 100%, or even 5 times, 10 times, 20 times, 50 times or 100 times or more increased or decreased level of reporter signal relative to the absence of a given modulator.

As used herein the term "inhibitor of a transcriptional regulatory sequence" refers to a compound or chemical moiety that causes a decrease in the amount of a reporter molecule or reporter molecule activity expressed from a given transcriptional regulatory sequence. As used herein, the term "decrease" when used in reference to the detection of a reporter molecule or reporter molecule activity means that detectable activity is reduced by at least 10%, 20%, 50%, 75%, or even 100% (i.e., no expression), relative to the amount detected in the absence of a given compound or chemical moiety. As used herein the term "candidate inhibitor" refers to a compound or chemical moiety being tested for inhibitory activity in an assay.

An advantage of the present invention is that it provides a method for the improved expression of a GFP in mammalian, particularly human cells both in vivo and in vitro. A further advantage of the present invention is that it provides a method of providing a humanized *R. Mulleri* GFP which, due to enhanced expression will produce a stronger fluorescent signal in cells in which it is expressed.

Further features and advantages of the invention will become more fully apparent in the following description of the embodiments and drawings thereof, and from the claims.

BRIEF DESCRIPTION OF THE DRAWINGS

FIG. 1 shows the coding sequence of humanized *R. mulleri* GFP, SEQ ID NO: 1. Residue number 93 can be T or C.

FIG. 2 shows the coding sequence of wild type *R. muller* GFP, SEQ ID NO: 2.

FIG. 3 shows the amino acid sequence of wild type *R. mulleri* GFP, SEQ ID NO: 3.

FIG. 4 shows a sequence alignment between non-humanized and humanized polynucleotide sequences encoding *R. mulleri* GFP. Vertical lines represent homology between the humanized and non-humanized genes. Gaps represent nucleotides that were altered to produce the hmGFP gene (i.e., the difference between SEQ ID NO: 1 and SEQ ID NO: 2). The valine at position 2 in the hmGFP sequence was inserted to accommodate an optimal Kozak translation initiation sequence.

DESCRIPTION

Figure 5:
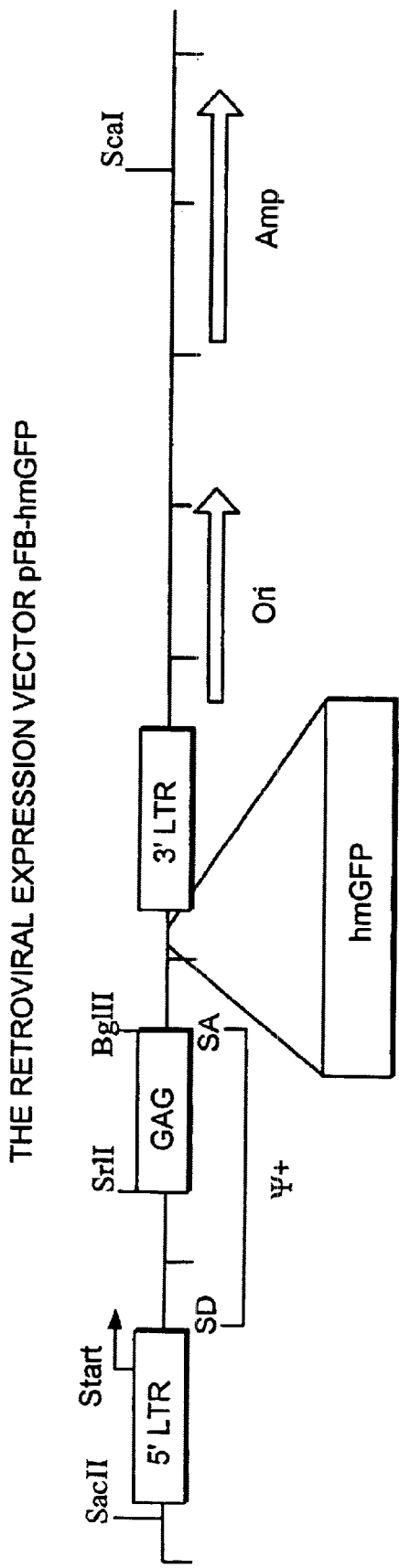
FIG. 5 shows the map of the retroviral expression vector pFB-hmGFP.

The invention is based upon the discovery of a humanized polynucleotide sequence encoding *R. mulleri* GFP.

Also disclosed herein are methods of using a humanized *R. mulleri* GFP gene to produce an *R. mulleri* GFP polypeptide, the methods comprising introducing an expression vector containing a humanized coding sequence for *R. mulleri* GFP into a cell, culturing the cell, and isolating the GFP polypeptide.

I How to Make a Humanized *R. mulleri* GFP Polynucleotide and Produce a *R. mulleri* GFP Polypeptide According to the Invention A number of methodologies were combined to provide the invention disclosed herein, including molecular, cellular and biochemical approaches. Polynucleotides encoding *R. mulleri* GFP or a variant GFP sequence to which a humanized sequence is desired are obtained in any of several different ways know to those of skill in the art, including direct chemical synthesis, library screening and PCR amplification. A. Polynucleotide sequence encoding wild type *R. mulleri* GFP.

The wild type polynucleotide sequence of *R. mulleri* has been previously disclosed in WO 99/49019, and is provided herein as SEQ ID NO:2. Accordingly one of skill in the art may generate a polynucleotide sequence encoding a wild type *R. mulleri* GFP by synthesizing the sequence of SEQ ID NO: 2, using methods known in the art (Alvarado-Urbina et al., (1981) Science 214:270). A polynucleotide sequence encoding wild type *R. mulleri* GFP may also be generated as described below.

1. *R. mulleri* cDNA Library Preparation.

Construction methods for libraries in a variety of different vectors, including, for example, bacteriophage, plasmids, and viruses capable of infecting eukaryotic cells are well known in the art. Any known library production method resulting in largely full-length clones of expressed genes may be used to provide a template for the isolation of wild type GFP-encoding polynucleotides from *R. mulleri*.

For the library used to isolate the GFP-encoding polynucleotides disclosed herein, the following method may be used. Poly(A) RNA can be prepared from *R. mulleri* organisms as described by Chomczynski, P. and Sacchi, N. (1987, Anal. Biochem. 162: 156–159). cDNA is prepared using the ZAP-cDNA Synthesis Kit (Stratagene cat.# 200400) according to the manufacturer's recommended protocols and inserted between the EcoR I and Xho I sites in the vector Lambda ZAP II. The resulting library contained 5×10[6] individual primary clones, with an insert size range of 0.5–3.0 kb and an average insert size of 1.2 kb. The library is amplified once prior to use as template for PCR reactions.

2. Isolation of *R. mulleri* GFP polynucleotide coding sequence by PCR.

The *R. mulleri* GFP coding sequence can be isolated by polymerase chain reaction (PCR) amplification of the sequence from within the cDNA library described herein. A large number of PCR methods are known to those skilled in the art. Thermal-cycled PCR (Mullis and Faloona, 1987, Methods Enzymol., 155: 335–350; see also, *PCR Protocols,* 1990, Academic Press, San Diego, Calif., USA for a review of PCR methods) uses multiple cycles of DNA replication catalyzed by a thermostable, DNA-dependent DNA polymerase to amplify the target sequence of interest. Briefly, oligonucleotide primers are selected such that they anneal on either side and on opposite strands of a sequence to be amplified. The primers are annealed and extended using a template dependent thermostable DNA polymerase, followed by thermal denaturation and annealing of primers to both the original template sequence and the newly-extended template sequences, after which primer extension is performed. Repeating such cycles results in exponential amplification of the sequences between the two primers.

In addition to thermal cycled PCR, there are a number of other nucleic acid sequence amplification methods that may be used to amplify and isolate a GFP-encoding polypeptide according to the invention from a *R. mulleri* cDNA library. These include, for example, isothermal 3SR (Gingeras et al., 1990, *Annales de Biologie Clinique*, 48(7): 498–501; Guatelli et al., 1990, *Proc. Natl. Acad. Sci. U.S.A.,* 87: 1874), and the DNA ligase amplification reaction (LAR), which permits the exponential increase of specific short sequences through the activities of any one of several bacterial DNA ligases (Wu and Wallace, 1989, *Genomics,* 4: 560). The contents of both of these references are incorporated herein in their entirety by reference.

To amplify a sequence encoding *R. mulleri* GFP from an *R. mulleri* cDNA library, the following approach can be taken. The *R. mulleri* GFP coding sequence can be amplified using 5' and 3' primers adjacent the coding region. Oligonucleotides may be purchased from any of a number of commercial suppliers (for example, Life Technologies, Inc., Operon Technologies, etc.). Alternatively, oligonucleotide primers may be synthesized using methods well known in the art, including, for example, the phosphotriester (see Narang, S. A., et al., 1979. *Meth. Enzymol.,* 68:90; and U.S. Pat. No. 4,356,270), phosphodiester (Brown, et al., 1979, *Meth. Enzymol.,* 68:109), and phosphoramidite (Beaucage, 1993, *Meth. Mol. Biol.,* 20:33) approaches. Each of these references is incorporated herein in its entirety by reference.

PCR is carried out in a 50 µl reaction volume containing 1× TaqPlus Precision buffer (Stratagene), 250 µM of each dNTP, 200 nM of each PCR primer, 2.5 U TaqPlus Precision enzyme (Stratagene) and approximately $3 \times 10^7$ lambda phage particles from the amplified cDNA library described above. Reactions can be carried out in a Robocycler Gradient 40 (Stratagene) as follows: 1 min at 95° C. (1 cycle),1 min at 95° C., 1 min at 53° C., 1 min at 72° C. 40 cycles) and 1 min at 72° C. (1 cycle). Reaction products are resolved on a 1% agarose gel, and a band of approximately 700 bp is then excised and purified using the StratalPrep DNA Gel Extraction Kit (Stratagene). Other methods of isolating and purifying amplified nucleic acid fragments are well known to those skilled in the art. The PCR fragment is then subcloned by digestion to completion with EcoRI and XhoI and insertion into the retroviral expression vector pFB (Stratagene) to create the vector pFB-rGFP. Both strands of the cloned GFP fragment are then completely sequenced. The coding polynucleotide and amino acid sequences are presented in FIGS. 2 and 3, respectively. The *R. mulleri* and *R. reniformis* GFP coding sequences are 83% homologous, and the proteins share 88% identical amino acid sequence.

3. Isolation of *R. mulleri* GFP-encoding polynucleotides by library screening.

An alternative method of isolating GFP-encoding polynucleotides according to the invention involves the screening of an expression library, such as a lambda phage expression library, for clones exhibiting fluorescence within the emission spectrum of GFP when illuminated with light within the excitation spectrum of GFP. In this way clones may be directly identified from within a large pool. Standard methods for plating lambda phage expression libraries and inducing expression of polypeptides encoded by the inserts are well established in the art. Screening by fluorescence excitation and emission is carried out as described herein below using either a spectrofluorometer or even visual identification of fluorescing plaques. With either method, fluorescent plaques are picked and used to re-infect fresh cultures one or more times to provide pure cultures, from which GFP insert sequences may be determined and subcloned.

As another alternative, if a sequence is available for the polynucleotide one wishes to obtain, the polynucleotide may be chemically synthesized by one of skill in the art. The same synthetic methods used for the preparation of oligonucleotide primers (described above) may be used to synthesize gene coding sequences for GFPs of the invention. Generally this would be performed by synthesizing several shorter sequences (about 100 nt or less), followed by annealing and ligation to produce the full length coding sequence.

B. Production of humanized polynucleotides encoding *R. mulleri*.

The present invention provides a modified nucleic acid sequence which represents a humanized form of *R. mulleri* which provides of enhanced expression of the encoded GFP polypeptide in human cells. To generate a humanized polynucleotide encoding *R. mulleri* GFP, useful in the present invention, the nucleic acid sequence encoding the polypeptide may be modified to enhance its expression in mammalian or human cells. The codon usage of *R. mulleri* is optimal for expression in *R. mulleri*, but not for expression in mammalian or human systems. Therefore, the adaptation of the sequence isolated from the sea pansy for expression in higher eukaryotes involves the modification of specific codons to change those less favored in mammalian or human systems to those more commonly used in these systems. This so-called "humanization" is accomplished by site-directed mutagenesis of the less favored codons as described herein below or as known in the art. The preferred codons for human gene expression are listed in Table 1. The codons in the table are arranged from left to right in descending order of relative use in human genes.

Humanized nucleotide sequences encoding *R. mulleri* may be generated by site directed mutagenesis. The humanized nucleotide sequences of SEQ ID NO: 1 may, of course, be varied slightly by altering several humanized codons to be non-preferential codons in a mammalian or human cell and such slight alterations are considered to be equivalent as long as they do not reduce the level of expression of the humanized gene in mammalian cells by more than 5 or 10% relative to the expression of the sequence of SEQ-ID NO: 1.

There are 64 possible combinations of the 4-DNA nucleotides in codon groups of 3, and the genetic code is redundant for many of the 20 amino acids. Each of the different codons for a given amino acid encodes the incorporation of that amino acid into a polypeptide. However, within a given species there tends to be a preference for certain of the redundant codons to encode a given amino acid. The "codon preference" of *R. mulleri* is different from that of humans (this codon preference is usually based upon differences in the level of expression of the tRNAs containing the corresponding anticodon sequences). Table 1 shows the preferred codons for human gene expression. A codon sequence is preferred for human expression if it occurs to the left of a given codon sequence in the table. Optimally, but not necessarily, less preferred codons in a non-human polynucleotide coding sequence are humanized by altering them to the condon most preferred for that amino acid in human gene expression.

TABLE 1

PREFERRED DNA CODONS FOR HUMAN USE

| Amino Acids | | | Codons Preferred in Human Genes |
|---|---|---|---|
| Alanine | Ala | A | GCC GCT GCA GCG |
| Cysteine | Cys | C | TGC TGT |

TABLE 1-continued

PREFERRED DNA CODONS FOR HUMAN USE

| Amino Acids | | | Codons Preferred in Human Genes |
|---|---|---|---|
| Aspartic acid | Asp | D | GAC GAT |
| Glutamic acid | Glu | E | GAG GAA |
| Phenylalanine | Phe | F | TTC TTT |
| Glycine | Gly | G | GGC GGG GGA GGT |
| Histidine | His | H | CAC CAT |
| Isoleucine | Ile | I | ATC ATT ATA |
| Lysine | Lys | K | AAG AAA |
| Leucine | Leu | L | CTG TTG CTT <u>CTA</u> <u>TTA</u> |
| Methionine | Met | M | ATG |
| Asparagine | Asn | N | AAC AAT |
| Proline | Pro | P | CCC CCT CCA CCG |
| Glutamine | Gln | Q | CAG CAA |
| Arginine | Arg | R | CGC AGG CGG AGA CGA CGT |
| Serine | Ser | S | AGC TCC TCT AGT TCA <u>TCG</u> |
| Threonine | Thr | T | ACC ACA ACT ACG |
| Valine | Val | V | GTG GTC GTT <u>GTA</u> |
| Tryprophan | Trp | W | TGG |
| Tyrosine | Tyr | Y | TAC TAT |

The codons at the left represent those most preferred for use in human genes, with human usage decreasing towards the right. Underlined codons are almost never used in human genes. C. Production of R. mulleri GFP polypeptides.

The production of R. mulleri GFP polypeptides (e.g., the polypeptide with the amino acid sequence of SEQ ID NO: 2) from recombinant vectors comprising humanized GFP-encoding polynucleotides of the invention may be effected in a number of ways known to those skilled in the art. For example, plasmids, bacteriophage or viruses may be introduced to prokaryotic or eukaryotic cells by any of a number of ways known to those skilled in the art. Following introduction of R. mulleri GFP-encoding polynucleotides to a prokaryotic or eukaryotic cell, expressed GFP polypeptides may be isolated using methods known in the art or described herein below. Useful vectors, cells, methods of introducing vectors to cells and methods of detecting and isolating GFP polypeptides are also described herein below.

1. Vectors Useful According to the Invention.

There is a wide array of vectors known and available in the art that are useful for the expression of GFP polypeptides according to the invention. The selection of a particular vector clearly depends upon the intended use of the GFP polypeptide. For example, the selected vector must be capable of driving expression of the polypeptide in the desired cell type, whether that cell type be prokaryotic or eukaryotic. Many vectors comprise sequences allowing both prokaryotic vector replication and eukaryotic expression of operably linked gene sequences.

Vectors useful according to the invention may be autonomously replicating, that is, the vector, for example, a plasmid, exists extrachromosonally and its replication is not necessarily directly linked to the replication of the host cell's genome. Alternatively, the replication of the vector may be linked to the replication of the host's chromosomal DNA, for example, the vector may be integrated into the chromosome of the host cell as achieved by retroviral vectors.

Vectors useful according to the invention preferably comprise sequences operably linked to the GFP coding sequences that permit the transcription and translation of the GFP sequence. Sequences that permit the transcription of the linked GFP sequence include a promoter and optionally also include an enhancer element or elements permitting the strong expression of the linked sequences. The term "transcriptional regulatory sequences" refers to the combination of a promoter and any additional sequences conferring desired expression characteristics (e.g., high level expression, inducible expression, tissue- or cell-type-specific expression) on an operably linked nucleic acid sequence.

The selected promoter may be any DNA sequence that exhibits transcriptional activity in the selected host cell, and may be derived from a gene normally expressed in the host cell or from a genie normally expressed in other cells or organisms. Examples of promoters include, but are not limited to the following: A) prokaryotic promoters—E. coli lac, tac, or trp promoters, lambda phage $P_R$ or $P_L$ promoters, bacteriophage T7, T3, Sp6 promoters, B. subtilis alkaline protease promoter, and the B. stearothermophilus maltogenic amylase promoter, etc.; B) eukaryotic promoters—yeast promoters, such as GAL1, GAL4 and other glycolytic gene promoters (see for example, Hitzeman et al., 1980, J. Biol. Chem. 255: 12073–12080; Alber & Kawasaki, 1982, J. Mol. Appl. Gen. 1: 419–434), LEU2 promoter (Martinez-Garcia et al., 1989, Mol Gen Genet. 217: 464–470), alcohol dehydrogenase gene promoters (Young et al., 1982, in Genetic Engineering of Microorganisms for Chemicals, Hollaender et al., eds., Plenum Press, NY), or the TPII promoter (U.S. Pat. No. 4,599,311); insect promoters, such as the polyhedrin promoter U.S. Pat. No. 4,745,05 1; Vasuvedan et al., 1992, FEBS Lett. 311: 7–11), the P10 promoter (Vlak et al., 1988, J. Gen. Virol. 69: 765–776), the Autographa californica polyhedrosis virus basic protein promoter (EP 397485), the baculovirus immediate-early gene promoter gene 1 promoter (U.S. Pat. Nos. 5,155,037 and 5,162,222), the baculovirus 39K delayed-early gene promoter (also U.S. Pat. Nos. 5,155,037 and 5,162,222) and the OpMNPV immediate early promoter 2; mammalian promoters—the SV40 promoter (Subramani et al., 1981, Mol. Cell. Biol. 1: 854–864), metallothionein promoter (MT-1; Palmiter et al., 1983, Science 222: 809–814), adenovirus 2 major late promoter (Yu et al.,1984, Nucl. Acids Res. 12: 9309–21), cytomegalovirus (CMV) or other viral promoter (Tong et al., 1998, Anticancer Res. 18: 719–725), or even the endogenous promoter of a gene of interest in a particular cell type.

A selected promoter may also be linked to sequences rendering it inducible or tissue-specific. For example, the addition of a tissue-specific enhancer element upstream of a selected promoter may render the promoter more active in a given tissue or cell type. Alternatively, or in addition, inducible expression may be achieved by linking the promoter to any of a number of sequence elements permitting induction by, for example, thermal changes (temperature sensitive), chemical treatment (for example, metal ion- or IPTG-inducible), or the addition of an antibiotic inducing agent (for example, tetracycline).

Regulatable expression is achieved using, for example, expression systems that are drug inducible (e.g., tetracycline, rapamycin or hormone-inducible). Drug-regulatable promoters that are particularly well suited for use in mammalian cells include the tetracycline regulatable promoters, and glucocorticoid steroid-, sex hormone steroid-, ecdysone-, lipopolysaccharide (LPS)- and isopropylthiogalactoside (IPTG)-regulatable promoters. A regulatable expression system for use in mammalian cells should ideally, but not necessarily, involve a transcriptional regulator that binds (or fails to bind) nonmammalian DNA motifs in response to a regulatory agent, and a regulatory sequence that is responsive only to this transcriptional regulator.

One inducible expression system that is well suited for the regulated expression of a GFP polypeptide of the invention, is the tetracycline-regulatable expression system, which is founded on the efficiency of the tetracycline resistance operon of *E. coli*. The binding constant between tetracycline and the tet repressor is high while the toxicity of tetracycline for mammalian cells is low, thereby allowing for regulation of the system by tetracycline concentrations in eukaryotic cell culture or within a mammal that do not affect cellular growth rates or morphology. Binding of the tet repressor to the operator occurs with high specificity.

Versions of the tet-regulatable system exist that allow either positive or negative regulation of gene expression by tetracycline. In the absence of tetracycline or a tetracycline analog, the wild-type bacterial tet repressor protein causes negative regulation of genes driven by promoters containing repressor binding elements from the tet operator sequences. Gossen & Bujard (1995, Science 268: 1766–1769; also International patent application No. WO 96/01313) describe a tet-regulatable expression system that exploits this positive regulation by tetracycline. In this system, tetracycline binds to a tet repressor fusion protein, rtTA, and prevents it from binding to the tet operator DNA sequence, thus allowing transcription and expression of the linked gene only in the presence of the drug.

This positive tetracycline-regulatable system provides one means of stringent temporal regulation of the GFP polypeptide of the invention (Gossen & Bujard, 1995, supra). The tet operator (tet O) sequence is now well known to those skilled in the art. For a review, the reader is referred to Hillen & Wissmann (1989) in Protein-Nucleic Acid Interaction, "Topics in Molecular and Structural Biology", eds. Saenger & Heinemann, (Macmillan, London), Vol. 10, pp 143–162. Typically the nucleic acid sequence encoding the GFP polypeptide is placed downstream of a plurality of let O sequences: generally 5 to 10 such tet O sequences are used, in direct repeats.

In addition to the tetracycline-regulatable systems, a number of other options exist for the regulated or inducible expression of a GFP polypeptide according to the invention. For example, the *E. coli* lac promoter is responsive to lac repressor (lacI) DNA binding at the lac operator sequence. The elements of the operator system are functional in heterologous contexts, and the inhibition of lacI binding to the lac operator by IPTG is widely used to provide inducible expression in both prokaryotic, and more recently, eukaryotic cell systems. In addition, the rapamycin-controlled transcriptional activator system described by Rivera et al. (1996, Nature Med. 2: 1028–1032) provides transcriptional activation dependent on rapamycin. That system has low baseline expression and a high induction ratio.

Another option for regulated or inducible expression of a GFP polypeptide involves the use of a heat-responsive promoter. Activation is induced by incubation of cells, transfected with a GFP construct regulated by a temperature-sensitive transactivator, at the permissive temperature prior to administration. For example, transcription regulated by a co-transfected, temperature sensitive transcription factor active only at 37° C. may be used if cells are first grown at, for example, 32° C., and then switched to 37° C. to induce expression.

Tissue-specific promoters may also be used to advantage in GFP-encoding constructs of the invention. A wide variety of tissue-specific promoters is known. As used herein, the term "tissue-specific" means that a given promoter is transcriptionally active (i.e., directs the expression of linked sequences sufficient to permit detection of the polypeptide product of the promoter) in less than all cells or tissues of an organism. A tissue specific promoter is preferably active in only one cell type, but may, for example, be active in a particular class or lineage of cell types (e.g., hematopoietic cells). A tissue specific promoter useful according to the invention comprises those sequences necessary and sufficient for the expression of an operably linked nucleic acid sequence in a manner or pattern that is essentially the same as the manner or pattern of expression of the gene linked to that promoter in nature. The following is a non-exclusive list of tissue specific promoters and literature references containing the necessary sequences to achieve expression characteristic of those promoters in their respective tissues; the entire content of each of these literature references is incorporated herein by reference. Examples of tissue specific promoters useful with the *R. mulleri* GFP of the invention are as follows: Bowman et al., 1995 Proc. Natl). Acad. Sci. USA 92,12115–12119 describe a brain-specific transferrin promoter; the synapsin I promoter is neuron specific (Schoch et al., 1996 J. Biol. Chem. 271, 3317–3323); the nestin promoter is post-mitotic netiron specific (Uetsuki et al., 1996 J. Biol. Chem. 271, 918–924); the neurofilament light promoter is neuron specific (Charron et al., 1995 J. Biol. Chem. 270, 30604–30610); the acetylcholine receptor promoter is neuron specific (Wood et al., 1995 J. Biol. Chem. 270, 30933–30940); the potassium channel promoter is high-frequency firing neuron specific (Gan et al., 1996 J. Biol. Chem 271, 5859–5865); the chromogranin A promoter is neuroendocrine cell specific (Wu et al., 1995 A. J. Clin. Invest. 96, 568–578); the Von Willebrand factor promoter is brain endothelium specific (Aird et al., 1995 Proc. Natl. Acad. Sci. USA 92, 4567–4571); the flt-1 promoter is endothelium specific (Morishita et al., 1995 J. Biol. Chem. 270, 27948–27953); the preproendothelin-1 promoter is endothelium, epithelium and muscle specific (Harats et al., 1995 J. Clin. Invest. 95, 1335–1344); the GLUT4 promoter is skeletal muscle specific (Olson and Pessin, 1995 J. Biol. Chem. 270, 23491–23495); the Slow/fast troponins promoter is slow/fast twitch myofibre specific (Corin et al., 1995 Proc. Natl. Acad. Sci. USA 92, 6185–6189); the β-Actin promoter is smooth muscle specific (Shimizu et al., 1995 J. Biol. Chem. 270. 7631–7643); the Myosin heavy chain promoter is smooth muscle specific (Kallmeier et al., 1995 J. Biol. Chem. 270, 30949–30957); the E-cadherin promoter is epithelium specific (Hennig et al., 1996 J. Biol. Chem. 271, 595–602); the cytokeratins promoter is keratinocyte specific (Alexander et al., 1995 B. Hum. Mol. Genet. 4, 993–999); the transglutaminase 3 promoter is keratinocyte specific (J. Lee et al., 1996 J. Biol. Chem. 271, 4561–4568); the bullous pemphigoid antigen promoter is basal keratinocyte specific (Tamai et al., 1995 J. Biol. Chem. 270, 7609–7614); the keratin 6 promoter is proliferating epidermis specific (Ramirez et al., 1995 Proc. Natl. Acad. Sci. USA 92,4783–4787); the collagen 1 promoter is hepatic stellate cell and skin/tendon fibroblast specific (Houglum et al., 1995 J. Clin. Invest. 96, 2269–2276); the type X collagen promoter is hypertrophic chondrocyte specific (Long & Linsenmayer, 1995 Hum. Gene Ther. 6, 419–428); the Factor VII promoter is liver specific (Greenberg et al., 1995 Proc. Natl. Acad. Sci. USA 92, 12347–1235); the fatty acid synthase promoter is liver and adipose tissue specific (Soncini et al., 1995. J. Biol. Chem. 270,. 30339–3034); the carbamoyl phosphate synthetase I promoter is portal vein hepatocyte and small intestine specific (Christoffels et al., 1995 J. Biol. Chem. 270, 24932–24940); the Na—K—Cl transporter promoter is kidney (loop of Henle) specific (Igarashi et al., 1996 J. Biol. Chem. 271, 666–9674); the scavenger receptor A promoter is macrophages and foam cell specific (Horvai et al., 1995 Proc. Natl. Acad. Sci. USA 92, 5391–5395); the glycoprotein IIb promoter is megakaryocyte and platelet specific (Block & Poncz, 1995 Stem Cells 13, 135–145); the γc chain promoter is hematopoietic cell specific (Markiewicz et al., 1996 J. Biol. Chem. 271, 14849–14855); and the CD11b promoter is mature myeloid cell specific (Dziennis et al., 1995 Blood 85, 319–329).

Any tissue specific transcriptional regulatory sequence known in the art may be used to advantage with a vector encoding *R. mulleri* GFP.

In addition to promoter/enhancer elements, vectors useful according to the invention may further comprise a suitable terminator. Such terminators include, for example, the human growth hormone terminator (Palmiter et al. 1983, supra), or, for yeast or fungal hosts, the TPI 1 (Alber & Kawasaki, 1982. supra) or ADH3 terminator (McKnight et al., 1985, EMBO J. 4: 2093–2099).

Vectors useful according to the invention may also comprise polyadenylation sequences (e.o., the SV40 or Ad5E1b poly(A) sequence), and translational enhancer sequences (e.g., those from Adenovirus VA RNAs). Further, a vector useful according to the invention may encode a signal sequence directing the recombinant polypeptide to a particular cellular compartment or, alternatively, may encode a signal directing secretion of the recombinant polypeptide.

Coordinate expression of different genes from the same promoter in a recombinant vector maybe achieved by using an IRES element, such as the internal ribosomal entry site of Poliovirus type 1 from pSBC-1 (Dirks et al., 1993, Gene 128:247–9). Internal ribosome binding site (IRES) elements are used to create multigenic or polycistronic messages. IRES elements are able to bypass the ribosome scanning mechanism of 5' methylated Cap-dependent translation and begin translation at internal sites (Pelletier and Sonenberg, 1988, Nature 334: 320–325). IRES elements from two members of the picanovirus family (polio and encephalomyocarditis) have been described (Pelletier and Sonenberg, 1988, supra), as well an IRES from a mammalian message (Macejak and Sarnow, 1991 Nature 353: 90–94). Any of the foregoing may be used in an *R. mulleri* GFP vector in accordance with the present invention.

IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. In this manner, multiple genes, one of which will be an *R. mulleri* GFP gene, can be efficiently expressed using a single promoter/enhancer to transcribe a single message. Any heterologus open reading frame can be linked to IRES elements. In the present context, this means any selected protein that one desires to express and any second reporter gene (or selectable marker gene). In this way, the expression of multiple proteins could be achieved, for example, with concurrent monitoring through GFP production.

A vector useful according to the invention may also comprise a selectable marker allowing identification of a cell that has received a functional copy of the GFP-encoding gene construct. In its simplest form, the GFP sequence itself, linked to a chosen promoter may be considered a selectable marker, in that illumination of cells or cell lysates with the proper wavelength of light and measurement of emitted fluorescence at the expected wavelength allows detection of cells that express the GFP construct. In other forms, the selectable marker may comprise an antibiotic resistance gene, such as the neomycin, bleomycin, zeocin or phleomycin resistance genes, or it may comprise a gene whose product complements a defect in a host cell, such as the gene encoding dihydrofolate reductase (DHFR), or, for example, in yeast, the Leu2 gene. Alternatively, the selectable marker may, in some cases be a luciferase gene or a chromogenic substrate-converting enzyme gene such as the β-galactosidase gene.

GFP-encoding sequences according to the invention may be expressed either as free-standing polypeptides or frequently as fusions with other polypeptides. It is assumed that one of skill in the art can, given the polynucleotide sequences disclosed herein (e.g., SEQ ID NO: 1) readily construct a gene comprising a sequence encoding *R. mulleri* GFP and a sequence comprising one or more polypeptides or polypeptide domains of interest. It is understood that the fusion of GFP coding sequences and sequences encoding a polypeptide of interest maintains the reading frame of all polypeptide sequences involved. As used herein, the term “polypeptide of interest” or “domain of interest” refers to any polypeptide or polypeptide domain one wishes to fuse to a GFP molecule of the invention. The fusion of a GFP polypeptide of the invention with a polypeptide of interest may be through linkage of the GFP sequence to either the N or C terminus of the fusion partner, or the GFP sequence may even be inserted in frame between the N and C termini of the polypeptide of interest, if so desired. Fusions comprising GFP polypeptides of the invention need not comprise only a single polypeptide or domain in addition to the GFP. Rather, any number of domains of interest may be linked in any way as long as the GFP coding region retains its reading frame and the encoded polypeptide retains fluorescence activity under at least one set of conditions. One non-limiting example of such conditions includes physiological salt concentration (i.e., about 90 mM), pH near neutral and 37° C.

a. Plasmid vectors.

Any plasmid vector that allows expression of a humanized GFP coding sequence of the invention in a selected host cell type is acceptable for use according to the invention. A plasmid vector useful in the invention may have any or all of the above-noted characteristics of vectors useful according to the invention. Plasmid vectors useful according to the invention include, but are not limited to the following examples: Bacterial—pQE70, pQE60, pQE-9 (Qiagen) pBs, phagescript, psiX174, pBluescript SK, pBsKS, pNH8a, pNH16a, pNH18a, pNH46a (Stratagene); pTrc99A, pKK223-3, pKK233-3, pDR540, and pRIT5 (Pharmacia); Eukaryotic—pWLneo, pSV2cat, pOG44, pXT1, pSG (Stratagene) pSVK3, pBPV, pMSG, and pSVL (Pharmacia). However, any other plasmid or vector may be used as long as it is replicable and viable in the host.

b. Bacteriophage vectors.

There are a number of well known bacteriophage-derived vectors useful according to the invention. Foremost among these are the lambda-based vectors, such as Lambda Zap II or Lambda-Zap Express vectors (Stratagene) that allow inducible expression of the polypeptide encoded by the insert. Others include filamentous bacteriophage such as the M13-based family of vectors.

c. Viral vectors.

A number of different viral vectors are useful according to the invention, and any viral vector that permits the introduction and expression of humanized sequences encoding *R. mulleri* GFP thereof in cells is acceptable for use in the methods of the invention. Viral vectors that can be used to deliver foreign nucleic acid into cells include but are not limited to retroviral vectors, adenoviral vectors, adeno-associated viral vectors, herpesviral vectors, and Semliki forest viral (alphaviral) vectors. Defective retroviruses are well characterized for use in gene transfer (for a review see Miller, A. D. (1990) Blood 76:271). Protocols for producing recombinant retroviruses and for infecting cells in vitro or in vivo with such viruses can be found in *Current Protocols in Molecular Biology,* Ausubel, F. M. et al. (eds.) Greene Publishing Associates, (1989), Sections 9.10–9.14, and other standard laboratory manuals.

In addition to retroviral vectors, Adenovirus can be manipulated such that it encodes and expresses a gene product of interest but is inactivated in terms of its ability to replicate in a normal lytic viral life cycle (see for example Berkner et al., 1988, BioTechniques 6:616; Rosenfeld et al., 1991, Science 252:431–434; and Rosenfeld et al., 1992, Cell 68:143–155). Suitable adenoviral vectors derived from the adenovirus strain Ad type 5 d1324 or other strains of adenovirus (e.g., Ad2, Ad3, Ad7 etc.) are well known to those skilled in the art. Adeno-associated virus (AAV) is a naturally occurring defective virus that requires another virus, such as an adenovirus or a herpes virus, as a helper virus for efficient replication and a productive life cycle. (For a review see Muzyczka et al., 1992, Curr. Topics in Micro. and Immunol. 158:97–129). An AAV vector such as that described in Traschin et al. (1985, Mol. Cell. Biol. 5:3251–3260) can be used to introduce nucleic acid into cells. A variety of nucleic acids have been introduced into different cell types using AAV vectors (see, for example, Hermonat et al., 1984, Proc. Nati. Acad. Sci. USA 81: 6466–6470; and Traschin et al., 1985, Mol. Cell. Biol. 4: 2072–2081).

Finally, the introduction and expression of foreign genes is often desired in insect cells because high level expression may be obtained, the culture conditions are simple relative to mammalian cell culture, and the post-translational modifications made by insect cells closely tesemble those made by mammalian cells. For the introduction of foreign DNA to insect cells, such as Drosophila S2 cells, infection with baculovirus vectors is widely used. Other insect vector systems include, for example, the expression plasmid pIZ/V5-His (InVitrogen) and other variants of the pIZ/V5 vectors encoding other tags and selectable markers. Insect cells are readily transfectable using lipofection reagents, and there are lipid-based transfection products specifically optimized for the transfection of insect cells (for example, from PanVera).

2. Host Cells Useful According to the Invention. Any cell into which a recombinant vector carrying a gene encoding *R. mulleri* GFP or humanized version may be introduced and wherein the vector is permitted to drive the expression of the GFP is useful according to the invention. That is, because of the wide variety of uses for the GFP molecules of the invention, any cell in which a GFP molecule of the invention may be expressed and preferably detected is a suitable host, wherein the host cell is preferably a mammalian cell and more preferably a human cell. Vectors suitable for the introduction of GFP-encoding sequences to host cells from a variety of different organisms, both prokaryotic and eukaryotic, are described herein above or known to those skilled in the art.

Host cells may be prokaryotic, such as any of a number of bacterial strains, or may be eukaryotic, such as yeast or other fungal cells, insect or amphibian cells, or mammalian cells including, for example, rodent, simian or human cells. Cells expressing GFPs of the invention may be primary cultured cells, for example, primary human fibroblasts or keratinocytes, or may be an established cell line, such as NIH3T3, 293T or CHO cells. Further, mammalian cells useful for expression of GFPs of the invention may be phenotypically normal or oncogenically transformed. It is assumed that one skilled in the art can readily establish and maintain a chosen host cell type in culture.

It is preferable that host cells of the present invention be human cells, as expression of a humanized GFP of the invention is particularly enhanced in human cells. Human cells which into which humanized *R. mulleri* GFP may be introduced include any cell in the human body. Introduction of humanized GFP, by any method described herein or known in the art, may be into human cells maintained in culture, human cell lines (i.e., HEK 293 cells), or may be into cells maintained in vivo in a human.

3. Introduction of GFP-Encoding Vectors to Host Cells.

GFP-encoding vectors may be introduced to selected host cells by any of a number of suitable methods known to those skilled in the art. For example, GFP constructs may be introduced to appropriate bacterial cells by infection, in the case of *E. coli* bacteriophage vector particles such as lambda or M13, or by any of a number of transformation methods for plasmid vectors or for bacteriophage DNA. For example, standard calcium-chloride-mediated bacterial transformation is still commonly used to introduce naked DNA to bacteria (Sambrook et al., 1989, *Molecular Cloning, A Laboratory Manual,* Cold Spring Harbor Laboratory Press, Cold Spring Harbor, N.Y.), but electroporation may also be used (Ausubel et al., 1988, *Current Protocols in Molecular Biology,* (John Wiley & Sons, Inc., New York, N.Y.)).

For the introduction of GFP-encoding constructs to yeast or other fungal cells, chemical transformation methods are generally used (e.g. as described by Rose et al., 1990, *Methods in Yeast Genetics,* Cold Spring Harbor Laboratory Press, Cold Spring Harbor, N.Y.). For transformation of *S. cerevisiae,* for example, the cells are treated with lithium acetate to achieve transformation efficiencies of approximately $10^4$ colony-forming units (transformed cells)/$\mu$g of DNA. Transformed cells are then isolated on selective media appropriate to the selectable marker used. Alternatively, or in addition, plates or filters lifted from plates may be scanned for GFP fluorescence to identify transformed clones.

For the introduction of *R. mulleri* GFP-encoding vectors to mammalian cells, the method used will depend upon the form of the vector. For plasmid vectors, humanized DNA encoding *R. mulleri* GFP may be introduced by any of a number of transfection methods, including, for example, lipid-mediated transfection ("lipofection"), DEAE-dextran-mediated transfection, electroporation or calcium phosphate precipitation. These methods are detailed, for example, in Current Protocols in Molecular Biology (Ausubel et al., 1988, John Wiley & Sons, Inc., NY, N.Y.).

Lipofection reagents and methods suitable for transient transfection of a wide variety of transformed and non-transformed or primary cells are widely available, making lipofection an attractive method of introducing constructs to eukaryotic, and particularly mammalian cells in culture. For example, LipofectAMINE™ (Life Technologies) or Lipo-Taxi™ (Stratagene) kits are available. Other companies offering reagents and methods for lipofection include Bio-Rad Laboratories, CLONTECH, Glen Research, InVitrogen, JBL Scientific, MBI Fermentas, PanVera, Promega, Quantum Biotechnologies, Sigma-Aldrich, and Wako Chemicals USA.

For the introduction of *R. mulleri* GFP-encoding vectors to insect cells, such as Drosophila Schneider 2 cells (S2) cells, Sf9 or Sf21cells, transfection is also performed by lipofection.

Following transfection with an *R. mulleri* GFP-encoding vector of the invention, eukaryotic (e.g., human) cells successfully incorporating the construct (intra- or extrachromosonally) may be selected, as noted above, by either treatment of the transfected population with a selection agent, such as an antibiotic whose resistance gene is encoded by the vector, or by direct screening using, for example, FACS of the cell population or fluorescence scanning of adherent cultures. Frequently, both types of screening may be used, wherein a negative selection is used to enrich for cells taking up the construct and FACS or fluorescence scanning is used to further enrich for cells expressing GFPs or to identify specific clones of cells, respectively. For example, a negative selection with the neomycin analog G418 (Life Technologies, Inc.) may be used to identify cells that have received the vector, and fluorescence scanning may be used to identify those cells or clones of cells that express the humanized *R. mulleri* GFP to the greatest extent.

4. Preparation of Antibodies Reactive with *R. mulleri* GFP

Antibodies that bind to a GFP polypeptide encoded by a polynucleotide of the invention are useful, for example, in protein purification and in protein association assays. An antibody useful in the invention may comprise a whole antibody, an antibody fragment, a polyfunctional antibody aggregate, or in general a substance comprising one or more specific binding sites from an antibody. The antibody fragment may be a fragment such as an Fv, Fab or F(ab')$_2$ fragment or a derivative thereof, such as a single chain Fv fragment. The antibody or antibody fragment may be non-recombinant, recombinant or humanized. The antibody may be of an immunoglobulin isotype, e.g., IgG, IgM, and so forth. In addition, an aggregate, polymer, derivative and conjugate of an immunoglobulin or a fragment thereof can be used where appropriate.

GFP-derived peptides used to induce specific antibodies preferably have an amino acid sequence consisting of at least five amino acids and more conveniently at least ten amino acids. It is advantageous for such peptides to be identical to a region of the natural *R. mulleri* GFP protein, and they may even contain the entire amino acid sequence of *R. mulleri* GFP (e.g., SEQ ID NO: 2).

For the production of antibodies, various hosts including goats, rabbits, rats, mice, etc., may be immunized by injection with peptides or polypeptides having sequences derived from the GFP pelypeptides of the invention. Depending on the host species, various adjuvants may be used to increase the immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol.

To generate polyclonal antibodies, the antigen (i.e., an *R. mulleri* GFP polypeptide, or peptide fragment derived therefrom) may be conjugated to a conventional carrier in order to increase its immunogenicity, and an antiserum to the peptide-carrier conjugate raised. Short stretches of amino acids corresponding to a GFP polypeptide of the invention may be fused, either by expression as a fusion product or by chemical linkage, with amino acids from another protein such as keyhole limpet hemocyanin or GST, with antibodies then being raised against the chimeric molecule. Coupling of a peptide to a carrier protein and immunizations may be performed as described in Dymecki et al., 1992, J. Biol. Chem., 267:4815. The serum can be titered against polypeptide antigen by ELISA or alternatively by dot or spot blotting (Boersma & Van Leeuwen, 1994, J. Neurosci. Methods, 51:317). A useful serum will react strongly with the appropriate peptides by ELISA, for example, following the procedures of Green et al., 1982, Cell, 28:477.

Techniques for preparing monoclonal antibodies are well known, and monoclonal antibodies may be prepared using an antigen, preferably bound to a carrier, as described by Arnleiter et al., 1981, Nature, 294:278. Monoclonal antibodies are typically obtained from hybridoma tissue cultures or from ascites fluid obtained from animals into which the hybridoma tissue was introduced. Monoclonal antibody-producing hybridomas (or polyclonal sera) can be screened for antibody binding to the target protein according to methods known in the art.

5. Purification of *R. mulleri* GFP

If necessary, *R. mulleri* GFP is purified from *R. mulleri* organisms as described by Ward and Cormier (1979, J. Biol. Chem. 254: 781–788) and by Matthews et al. (1977, Biochemistry 16: 85–91), the contents of both of which are herein incorporated by reference. Similar procedures may be applied by one of skill in the art to bacterially expressed *R. mulleri* GFP following freeze-thaw lysis and preparation of a clarified lysate by centrifugation at 14,000×g. Briefly, the methods employed by Matthews et al. and Ward and Cormier involve successive chromatography over DEAE-cellulose, Sephadex G-100, and DTNB (5, 5'-dithiobis(2-nitrobenzoic acid))-Sepharose columns, and dialysis against 1 mM Tris (pH 8.0), 0.1 mM EDTA. The dialyzed fractions containing GFP (identified by fluorescence) are then acid treated to precipitate contaminants, followed by neutralization of the supernatant, which is lyophilized. Low salt (10 mnM to 1 mM initially) and pH ranging from 7.5 to.8.5 are critical to maintaining activity upon lyophilization. The lyophilized sample is re-suspended in water, immediately centrifuged to remove less-soluble contaminants and applied to a Sephadex G-75 column. GFP is eluted in 1.0 mM Tris (p8.0), 0.1 mM EDTA. Samples are concentrated by partial lyophilization and dialyzed against 5 mM sodium acetate, 5 mM imidazole, 1 nM EDTA, pH 7.5, followed by chromatography over a DEAE-BioGel-A column equilibrated in the same dialysis buffer. GFP is eluted with a continuous acidic gradient from pH 6.0 to 4.9 in the same acetate/imidizole buffer. Following dialysis of GFP-containing fractions against 1.0 mM Tris-HCl, 0.1 mM EDTA, pH 8.0, the sample is partially lyophilized to concentrate and passed over a Sephadex G-75 (Superfine) column. The GFP-containing fractions are then loaded onto a DEAE-BioGel A column in Tris/EDTA buffer at pH 8.0, followed by elution in a continuous alkaline gradient from pH 8.5 to 10.5 formed with 20 mM glycine, 5 mM Tris-HCI and 5 mM EDTA. GFP-containing fractions contain essentially homogeneous *R. mulleri* GFP.

In screening applications requiring less pure GFP preparations, recombinant *R. mulleri* can be purified from bacteria as follows. Bacteria transformed with a recombinant GFP-encoding vector of the invention are grown in Luria-Bertani medium containing the appropriate selective antibiotic (e.g., ampicillin at 50 µg/ml). If the vector permits, recombinant polypeptide expression is induced by the addition of the appropriate inducer (e.g., IPTG at 1 mM). Bacteria are harvested by centrifugation and lysed by freeze-thaw of the cell pellet. Debris is removed by centrifugation at 14,000×g, and the supernatant is loaded onto a Sephadex G-75 (Pharmacia, Piscataway, N.J.) column equilibrated with 10 mM phosphate buffered saline, pH 7.0. Fractions containing GFP are identified by fluorescence emission at 500 nm when excited by 500 nm light.

II. How to Use Humanized Polynucleotides Encoding *R. mulleri* GFP According to the Invention Humanized polynucleotide sequences encoding *R. mulleri* GFP are useful in a number of different ways. Generally, a polynucleotide sequence encoding *R. mulleri* GFP is useful in any process or assay that can be performed with *A.*

*victoria* GFP. Further, because of its ehnhanced expression in mammalian cells and fluorescent intensity, a humanized polynucleotide sequence encoding *R. mulleri* GFP is useful in processes and assays beyond those that can be performed with *A. victoria* GFP.

Humanized polynucleotide sequences encoding *R. mulleri* GFP may be used as selectable markers for the identification of cells transfected or infected with a gene transfer vector. In this aspect, cells transfected with a humanized construct encoding GFP may be identified over a background of non-transfected or infected cells by illumination of the cells with light within the excitation spectrum and detection of fluorescent emission in the emission spectrum of the GFP.

Humanized *R. mulleri* GFP genes can be used to identify transformed mammalian cells (e.g., by fluorescence-activated cell sorting (FACS) or fluorescence microscopy), particularly human cells, to measure gene expression in vitro and in vivo, to label specific cells in multicellular organisms (e.g., to study cell lineages), to label and locate fusion proteins, and to study intracellular protein trafficking.

*R. mulleri* GFPs may also be used for standard biological applications. For example, they may be used as molecular weight markers on protein gels and Western blots, in calibration of fluorometers and FACS equipment and as a marker for micro injection into cells and tissues. In methods to produce fluorescent molecular weight markers, an *R. mulleri* GFP gene sequence is fused to one or more DNA sequences that encode proteins having defined amino acid sequences, and the fusion proteins are expressed from an expression vector. Expression results in the production of fluorescent proteins of defined molecular weight or weights that may be used as markers.

Preferably, purified fluorescent proteins are subjected to size-fractionation, such as by using a gel. A determination of the molecular weight of an unknown protein is then made by compiling a calibration curve from the fluorescent standards and reading the unknown molecular weight from the curve.

A. Use of humanized polynucleotides encoding *R. mulleri* GFP in the identification of transfected cells.

A humanized polynucleotide sequence encoding *R. mulleri* GFP may be introduced as a selectable marker to identify transfected mammalian cells from a background of non-transfected cells. Alternatively, humanized *R. mulleri* GFP transfection may be used to pre-label isolated cells or a population of similar cells prior to exposing the cells to an environment in which different cell types are present. Detection of GFP in only the original cells allows the location of such cells to be determined and compared with the total population.

Mammalian cells that have been transfected with exogenous DNA can be idenitified with polynucleotide sequence encoding *R. mulleri* GFPs of the invention without creating a fusion protein. The method relies on the identification of cells that have received a plasmid or vector that comprises at least two transcriptional or translational units. A first unit will encode and direct expression of the desired protein, while the second unit will direct expression of humanized polynucleotide sequences encoding *R. mulleri* GFP. Co-expression of GFP from the second transcriptional or translational unit ensures that cells containing the vector are detected and differentiated from cells that do not contain the vector.

The humanized *R. mulleri* GFP sequences of the invention may also be fused to a DNA sequence encoding a selected protein in order to directly label the encoded protein with GFP. Expressing such an *R. mulleri* GFP fusion protein in a human cell results in the production of fluorescently-tagged proteins that can be readily detected. This is useful in confirming that a protein is being produced by a chosen host cell. It also allows the location of the selected protein to be determined, whether this represents a natural location or whether the protein has been artificially targeted to another location.

B. Use of humanized polynucleotides encoding *R. mulleri* for analysis of transcriptional regulatory sequences.

The humanized *R. mulleri* GFP genes of the invention allow a range of transcriptional regulatory sequences to be tested for their suitability for use with a given gene, cell, or system, but preferably for use with mammalian cells, preferably human cells. This applies to in vitro uses, such as in identifying a suitable transcriptional regulatory sequence for use in recombinant expression and high level protein production, as well as in vivo uses, such as in pre-clinical testing or in gene therapy in human subjects.

In order to analyze a transcriptional regulatory sequence, one must first establish a control cell or system. In the control, a positive result is established by using a known and effective promoter, such as the CMV promoter. To test a candidate transcriptional regulatory sequence, another cell or system, or a second population of the same cell type used as control, is established in which all conditions are the same except for there being different transcriptional regulatory sequences in the expression vector or genetic construct. After running the assay for the same period of time and under the same conditions as in the control, the expression levels of polynucleotide sequences encoding GFP are determined. This allows one to make a comparison of the strength or suitability of the candidate transcriptional regulatory sequence with the standard or control transcriptional regulatory sequence.

Transcriptional regulatory sequences that can be tested in this manner also include candidate tissue-specific promoters and candidate-inducible promoters. Testing of tissue-specific promoters allows the identification of optimal transcriptional regulatory sequences for use with a given cell. Again, this is useful both in vitro and in vivo. Optimizing the combination of a given transcriptional regulatory sequence and a given cell type in recombinant expression and protein production is often necessary to ensure that the highest possible expression levels are achieved.

The humanized GFP encoded by a regulatory sequence testing construct may optionally have a secretion signal fused to it, such that GFP secreted to the medium is detected.

The use of tissue-specific promoters and inducible promoters is particularly powerful in vivo embodiments. When used in the context of expressing a therapeutic gene in an human, the use of such transcriptional regulatory sequences allows expression only in a given tissue or tissues, at a given site and/or under defined conditions. Achieving tissue-specific expression is particularly important in certain gene therapy applications, such as in the expression of a cytotoxic agent, as is often employed in approaches to the treatment of cancer. In expressing other therapeutic genes with a beneficial effect, rather than a cytotoxic effect, tissue-specific expression is also preferred since it can optimize the effect of the treatment. Appropriate tissue-specific and inducible transcriptional regulatory sequences are known to those of skill in the art, or, for example, described herein above.

C. Use of humanized polynucleotide sequences encoding *R. mulleri* GFP in assays for compounds that modulate transcription.

Humanized polynucleotide sequences encoding *R. mulleri* GFP are useful in screening assays to detect compounds that modulate transcription. In this aspect of the invention, humanized *R. mulleri* GFP coding sequences are positioned downstream of a promoter that is known to be inducible by the agent that one wishes to detect. Expression of GFP in the cells will normally be silent, and is activated by exposing the cell to a composition that contains the selected agent. In using a promoter that is responsive to, for example, a lipid soluble transcriptional modulator, a toxin, a hormone, a cytokine, a growth factor or other defined molecule, the presence the particular defined molecule can be determined. For example, an estrogen-responsive regulatory sequence may be linked to GFP in order to test for the presence of estrogen in a sample.

It will be clear to one of skill in the art that any of the detection assays may be used in the context of screening for agents that inhibit, suppress or otherwise down regulate gene expression from a given transcriptional regulatory sequence. Such negative effects are detectable by decreased GFP fluorescence that results when gene expression is down-regulated in response to the presence of an inhibitory agent.

D. Use of humanized polynucleotide sequences encoding *R. mulleri* GFP in FACS analyses.

Many conventional FACS methods require the use of fluorescent dyes conjugated to purified antibodies. Fusion proteins tagged with a fluorescent label are preferred over antibodies in FACS applications because the cells do not have to be incubated with the fluorescent-tagged reagent and because there is no background due to nonspecific binding of an antibody conjugate. GFP is particularly suitable for use in FACS as fluorescence is stable and species-independent and does not require any substrates or cofactors.

As with other expression embodiments, a desired protein may be directly labeled with GFP by preparing a fusion protein comprising a humanized polynucleotide sequence encoding GFP for expression in a cell; preferably a humanized GFP fusion protein in a human cell. A humanized polynucleotide sequence encoding GFP can also be co-expressed from a second transcriptional or translational unit within the expression vector that expresses desired protein, as described above. Cells expressing the GFP-tagged protein or cells co-expressing GFP are then detected and sorted by FACS analysis.

F. Other uses of humanized polynucleotide sequences encoding *R. mulleri* GFP fusion proteins.

Humanized *R. mulleri* GFP genes can be used as one portion of a fusion protein, allowing the location of the tagged protein to be identified. Fusions of GFP with an exogenous protein should preserve both the fluorescence of GFP and functions of the host protein, such as physiological functions and/or targeting functions.

Both the amino and carboxyl termini of GFP may be fused to virtually any desired protein to create an identifiable GFP-fusion, and fusion may be mediated by a linker sequence if necessary to preserve the function of the fusion partner. However, it is preferable that the protein fused to GFP not possess fluorescent properties of its own (e.g., a luciferase protein) to prevent interference in screening for GFP expression.

*R. mulleri* GFP fusions are useful for subcellular localization studies. Localization studies have previously been carried out by subcellular fractionation and by imnunofluorescence. However, these techniques can give only a static representation of the position of the protein at one instant in the cell cycle. In addition, artifacts can be introduced when cells are fixed for immunofluorescence. Using GFP to visualize proteins in living cells, which allows proteins to be followed throughout the cell cycle in an individual cell, is thus an important technique.

EXAMPLES

Example 1

Comparison of Expression of Humanized Versus Wild Type Genes Encoding *R. mulleri* GFP The humanized *R. mulleri* GFP coding sequence can be tested for expression in several human, rodent and monkey cell lines. Fluoresence levels are expected to be substantially higher for the humanized rGFP (hrGFP) gene compared with that for rGFP. In a direct comparison between cell populations harboring single copy proviral expression cassettes encoding either hrGFP or the humanized, red-shifted Aequorea GFP (EGFP), relative fluorescence intensity is expected to be comparable between the two genes.

Viral Transduction

One day prior to transduction, 293 cells (human) or CHO cells (hamster) are plated in DMEM supplemented with 10% FBS at $1\times10^5$ cells/well in a 6 well tissue culture dish. The following day the viral supernatants are serially diluted in DMEM +10% FBS to a final volume of 1.0 ml/sample, and supplemented with DEAE-Dextran (Sigma, St. Louis, Mo., catalog #D-9885) to a final concentration of 10 $\mu$g/ml. Culture medium is then removed from the target cells and replaced with 1 ml of viral dilution. Each diluted viral sample is applied to a well containing the target cells, and incubated for 3 h, after which 1 ml of pre-warmed DMEM +10% FBS can be added to each well, and the plates are then incubated for-2 d. After 2 d the plates are washed 2×with PBS, trypsinized, pelleted by centrifugation, and resuspendedin 1.0 ml PBS. Cell suspensions can be stored on ice and analyzed by Fluorescence Activated Cell Sorting (FACS) within one hour. FACS analysis may optionally be performed by Cytometry Research Services, (Sorrento Valley, Calif.).

Comparison of rGFP and hmGFP Expression in Vivo

To determine whether the sequence alterations introduced into the *R. mulleri* GFP gene resulted in enhanced expression, the hmGFP coding sequence may be inserted into the vector pFB, and the resulting vector pFB-hmGFP is then transfected side-by-side with the parental vector pFB-rGFP gene into CHO cells. Visual inspection of the transfected cells by fluorescence microscopy (excitation 450–490 nm; emission 520 nm) can be performed. CHO cells can then be infected with virus derived from the two vectors at equivalent multiplicities of infection (MOI), and two days following infection the transduced cells can be analyzed by fluorescence-activated cell sorting (FACS; excitation 488 nm, emission 515–545 nm).

The relative fluorescence can be compared from cells harboring single-copy proviral integrants encoding rGFP, hrGFP or EGFP. 293 cells are infected at low MOI, and two days post-infection the fluoresence levels are analysed by FACS. In the transduced populations, the overall fluorescence intensity of the populations is expected to be comparable for the hrGFP and EGFP expression vectors. Fluorescence for rGFP is expected to be significantly lower than for the latter two genes. Similar results are anticipated for experiments involving the transduction of HeLa, CHO, COS7 and NIH3T3 cells.

Example 2

Expression of Humanized *R. mulleri* GFP in Human Cells

Enhanced Expression

Figure 6:
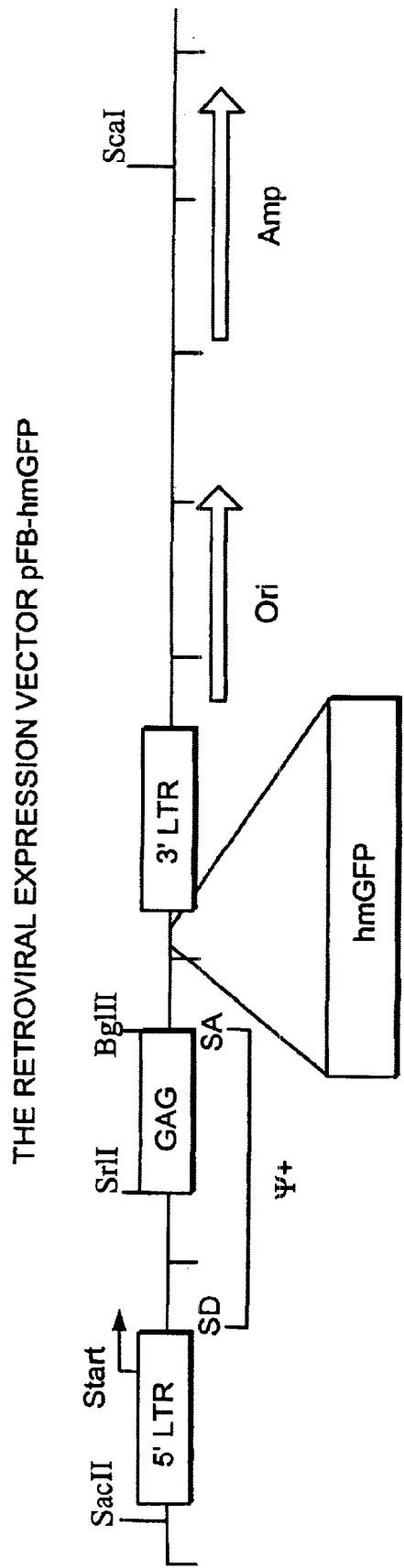
FIG. 6 shows the map of the retroviral expression vector pCFB-hmGFP.
Figure 7:
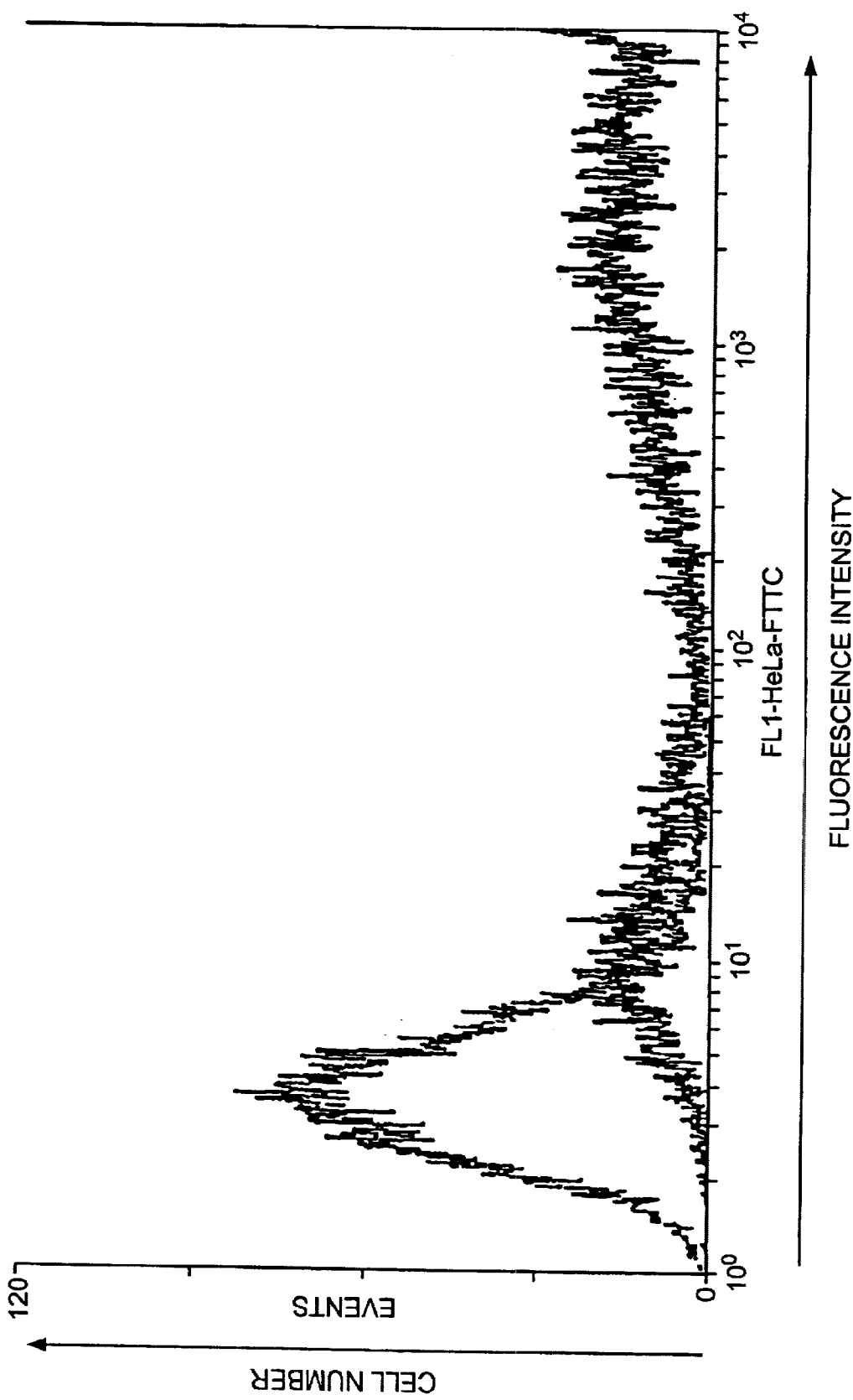
FIG. 7 shows the results of FACS sorting of HeLa cells transduced with a hmGFP-expressing retrovirus.

To confirm enhanced expression of a humanized *R. mulleri* GFP nucleic acid sequence in human cells, nucleic acid encoding the humanized sequence was expressed in human HeLa cells. Production of viral particles encoding the humanized GFP for transduction of human cells was carried out by co-transfecting 293 cells with 3 µg each of the retroviral packaging vectors pVPack-GP, pVPack-VSV-G (Stratagene) and pCFB-hmGFP (humanized *R. mulleri* GFP; FIG. 6). The transfections were carried out according to Pear et al. (1997, *Methods in Molecular Medicine: Gene Therapy Protocols*, Robbind (Ed.) Humana Press, Totawa, N.J.), but modified by using the MBS Transfection Kit (Stratagene). Subsequently, $2 \times 10^5$ HeLa cells were infected with tissue culture supernatant containing no virus (FIG. 7 gray curve) or containing virus prepared using pCFB-hmGFP (FIG. 7, black curve). After 72 hours, cells were trypsinized and analyzed by FACS (Cytometry Research Services, Sorrento Valley, Calif.) using standard FITC filters (FIG. 7).

Fluroescence Spectra

Figure 8:
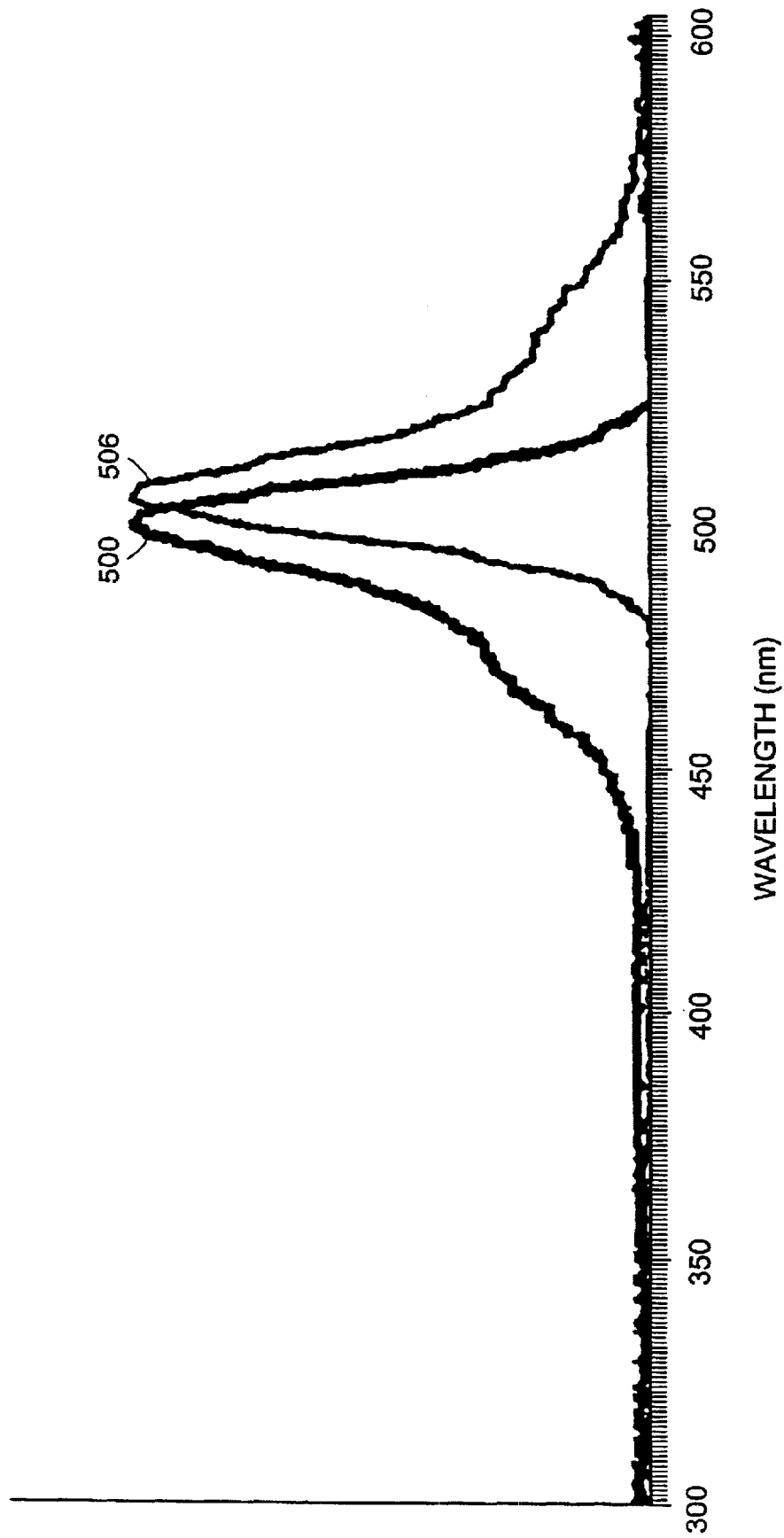
FIG. 8 shows the fluorescence spectra of HeLa cell extracts containing hmGFP.

To confirm that the fluorescence spectra for the cloned, humanized gene encoding *R. mulleri* GFP is identical to that previously reported for the native protein, the fluorescence spectra of human cells expressing the humanized GFP was examined. HeLa cells transduced with the hmGFP-expressing retrovirus, described above, were lysed in PBS by three cycles of freeze-thawing using liquid nitrogen and a 37° C. water bath. The lysates were cleared by high-speed centrifugation, and the supernatants were then used for spectral analysis. Excitation and emission spectral analysis was determined using a Shimadzu RF-1501 Spectrofluorophotometer. Excitation and emission scans were performed on equal amounts of total protein prepared from transfected or untransfected HeLa cells. Background fluorescence was subtracted from the scans of the GFP-containing (transfected) extract by normalization to the scans of the untransfected extracts. FIG. 8 shows that the fluorescence spectra of cell extracts containing hmGFP is the same as that for native *R. mulleri* GFP, with the major excitation peak at 500 nm and the major emission peak at 506 nm.

Other Embodiments

Other embodiments will be evident to those of skill in the art. It should be understood that the foregoing detailed description is provided for clarity only and is merely exemplary. The spirit and scope of the present invention are not limited to the above examples, but are encompassed by the following claims.

---

We claim:

1. A humanized polynucleotide encoding *R. mulleri* GFP comprising the sequence of SEQ ID NO: 1, wherein the nucleotide at position 93 is either a T or C.

2. A recombinant vector comprising a polynucleotide of claim 1.

3. An isolated cell containing a recombinant vector of claim 2.

* * * * *

SEQUENCE LISTING

```
<160> NUMBER OF SEQ ID NOS: 3

<210> SEQ ID NO 1
<211> LENGTH: 720
<212> TYPE: DNA
<213> ORGANISM: Artificial Sequence
<220> FEATURE:
<223> OTHER INFORMATION: Humanized R. mulleri polynucleotide
<221> NAME/KEY: misc_feature
<222> LOCATION: (1)..(720)
<223> OTHER INFORMATION: Humanized DNA sequence

<400> SEQUENCE: 1
atggtgagca agcagatcct gaagaacacc tgcctgcagg aggtgatgag ctacaaggtg      60
aacctggagg gcatcgtgaa caaccacgtg ttcaccatgg agggctgcgg caagggcaac     120
atcctgttcg gcaaccagct ggtgcagatc cgcgtgacca agggcgcccc cctgcccttc     180
gccttcgaca tcgtgagccc cgccttccag tacggcaacc gcaccttcac caagtacccc     240
aacgacatca gcgactactt catccagagc ttccccgccg gcttcatgta cgagcgcacc     300
ctgcgctacg aggacggcgg cctggtggag atccgcagcg acatcaacct gatcgaggac     360
aagttcgtgt accgcgtgga gtacaagggc agcaacttcc ccgacgacgg ccccgtgatg     420
cagaagacca tcctgggcat cgagcccagc ttcgaggcca tgtacatgaa caacggcgtg     480
ctggtgggcg aggtgatcct ggtgtacaag ctgaacagcg gcaagtacta cagctgccac     540
atgaagaccc tgatgaagag caagggcgtg gtgaaggagt tcccctccta ccacttcatc     600
cagcaccgcc tggagaagac ctacgtggag gacggcggct tcgtggagca gcacgagacc     660
gccatcgccc agatgaccag catcggcaag cccctgggca gcctgcacga gtgggtgtaa     720

<210> SEQ ID NO 2
<211> LENGTH: 1021
```

-continued

```
<212> TYPE: DNA
<213> ORGANISM: Renilla muelleri
<220> FEATURE:
<221> NAME/KEY: exon
<222> LOCATION: (259)..(976)

<400> SEQUENCE: 2
ggttatacac aagtgtatcg cgtatctgca gacgcatcta gtgggattat tcgagcggta       60
gtatttacgt cagacctgtc taatcgaaac cacaacaaac tcttaaaata agccacattt      120
acataatatc taagagacgc ctcatttaag agtagtaaaa atataatata tgatagagta      180
tacaactctc gccttagaca gacagtgtgc aacagagtaa ctcttgttaa tgcaatcgaa      240
agcgtcaaga gagataag atg agt aaa caa ata ttg aag aac act tgt tta       291
                    Met Ser Lys Gln Ile Leu Lys Asn Thr Cys Leu
                     1               5                      10 caa gaa gta atg tcg tat aaa gta aat ctg gaa gga att gta aac aac       339
Gln Glu Val Met Ser Tyr Lys Val Asn Leu Glu Gly Ile Val Asn Asn
             15                  20                  25 cat gtt ttt aca atg gag ggt tgc cgc aaa cgg aat att tta ttc ggc       387
His Val Phe Thr Met Glu Gly Cys Arg Lys Arg Asn Ile Leu Phe Gly
         30                  35                  40 aat caa ctg gtt cac att cgt gtc acg aaa ggg ggc cca ctg cct ttt       435
Asn Gln Leu Val His Ile Arg Val Thr Lys Gly Gly Pro Leu Pro Phe
     45                  50                  55 gca ttt gat att gtg tca cca gct ttt caa tat ggc aac cgt act ttc       483
Ala Phe Asp Ile Val Ser Pro Ala Phe Gln Tyr Gly Asn Arg Thr Phe
 60                  65                  70                  75 acg aaa tat ccg aat gat ata tca gat tat ttt ata caa tca ttt cca       531
Thr Lys Tyr Pro Asn Asp Ile Ser Asp Tyr Phe Ile Gln Ser Phe Pro
                 80                  85                  90 gca gga ttt atg tat gaa cga aca tta cgt tac gaa gat ggc gga ctt       579
Ala Gly Phe Met Tyr Glu Arg Thr Leu Arg Tyr Glu Asp Gly Gly Leu
             95                 100                 105 gtt gaa att cgt tca gat ata aat tta ata gaa gac aag ttc gtc tac       627
Val Glu Ile Arg Ser Asp Ile Asn Leu Ile Glu Asp Lys Phe Val Tyr
         110                 115                 120 aga gtg gaa tac aaa ggt agt aac ttc cca gat gat ggt ccc gtc atg       675
Arg Val Glu Tyr Lys Gly Ser Asn Phe Pro Asp Asp Gly Pro Val Met
     125                 130                 135 cag aag act atc tta gga ata gag cct tca ttt gaa gcc atg tac atg       723
Gln Lys Thr Ile Leu Gly Ile Glu Pro Ser Phe Glu Ala Met Tyr Met
140                 145                 150                 155 aat aat ggc gtc ttg gtc ggc gaa gta att ctt gtc tat aaa cta aac       771
Asn Asn Gly Val Leu Val Gly Glu Val Ile Leu Val Tyr Lys Leu Asn
                 160                 165                 170 tct ggg aaa tat tat tca tgt cac atg aaa aca tta atg aag tcg aaa       819
Ser Gly Lys Tyr Tyr Ser Cys His Met Lys Thr Leu Met Lys Ser Lys
             175                 180                 185 ggt gta gta aag gag ttt cct tcg tat cat ttt att caa cat cgt ttg       867
Gly Val Val Lys Glu Phe Pro Ser Tyr His Phe Ile Gln His Arg Leu
         190                 195                 200 gaa aag act tac gta gaa gac ggg ggg ttc gtt gaa cag cat gag act       915
Glu Lys Thr Tyr Val Glu Asp Gly Gly Phe Val Glu Gln His Glu Thr
     205                 210                 215 gct att gct caa atg aca tct ata gga aaa cca cta gga tcc tta cac       963
Ala Ile Ala Gln Met Thr Ser Ile Gly Lys Pro Leu Gly Ser Leu His
220                 225                 230                 235 gaa tgg gtt taa a cacagttaca ttacttttc caattcgtgt ttcatgtcaa         1016
Glu Trp Val
```

-continued

```
                                                                   1021
ataat
```

<210> SEQ ID NO 3
<211> LENGTH: 238
<212> TYPE: PRT
<213> ORGANISM: Renilla muelleri

<400> SEQUENCE: 3

```
Met Ser Lys Gln Ile Leu Lys Asn Thr Cys Leu Gln Glu Val Met Ser
1               5                   10                  15

Tyr Lys Val Asn Leu Glu Gly Ile Val Asn Asn His Val Phe Thr Met
            20                  25                  30

Glu Gly Cys Arg Lys Arg Asn Ile Leu Phe Gly Asn Gln Leu Val His
        35                  40                  45

Ile Arg Val Thr Lys Gly Gly Pro Leu Pro Phe Ala Phe Asp Ile Val
    50                  55                  60

Ser Pro Ala Phe Gln Tyr Gly Asn Arg Thr Phe Thr Lys Tyr Pro Asn
65                  70                  75                  80

Asp Ile Ser Asp Tyr Phe Ile Gln Ser Phe Pro Ala Gly Phe Met Tyr
                85                  90                  95

Glu Arg Thr Leu Arg Tyr Glu Asp Gly Gly Leu Val Glu Ile Arg Ser
            100                 105                 110

Asp Ile Asn Leu Ile Glu Asp Lys Phe Val Tyr Arg Val Glu Tyr Lys
        115                 120                 125

Gly Ser Asn Phe Pro Asp Asp Gly Pro Val Met Gln Lys Thr Ile Leu
    130                 135                 140

Gly Ile Glu Pro Ser Phe Glu Ala Met Tyr Met Asn Asn Gly Val Leu
145                 150                 155                 160

Val Gly Glu Val Ile Leu Val Tyr Lys Leu Asn Ser Gly Lys Tyr Tyr
                165                 170                 175

Ser Cys His Met Lys Thr Leu Met Lys Ser Lys Gly Val Val Lys Glu
            180                 185                 190

Phe Pro Ser Tyr His Phe Ile Gln His Arg Leu Glu Lys Thr Tyr Val
        195                 200                 205

Glu Asp Gly Gly Phe Val Glu Gln His Glu Thr Ala Ile Ala Gln Met
    210                 215                 220

Thr Ser Ile Gly Lys Pro Leu Gly Ser Leu His Glu Trp Val
225                 230                 235
```